US008748565B2

(12) United States Patent  
Brandt et al.

(10) Patent No.: US 8,748,565 B2  
(45) Date of Patent: Jun. 10, 2014

(54) PHARMACOLOGICALLY ACTIVE ANTIVIRAL PEPTIDES AND METHODS OF THEIR USE

(75) Inventors: Curtis R. Brandt, Stoughton, WI (US); Hermann Bultmann, Madison, WI (US)

(73) Assignee: Wisconsin Alumni Reseach Foundation, Madison, WI (US)

( * ) Notice: Subject to any disclaimer, the term of this patent is extended or adjusted under 35 U.S.C. 154(b) by 1455 days.

(21) Appl. No.: 12/061,378

(22) Filed: Apr. 2, 2008

(65) Prior Publication Data

US 2012/0157376 A1   Jun. 21, 2012

Related U.S. Application Data

(62) Division of application No. 09/777,560, filed on Feb. 6, 2001, now Pat. No. 7,371,809.

(60) Provisional application No. 60/180,823, filed on Feb. 7, 2000, provisional application No. 60/184,057, filed on Feb. 22, 2000.

(51) Int. Cl.
*A61K 39/00* (2006.01)
*A61K 38/00* (2006.01)

(52) U.S. Cl.
USPC ............... 530/300; 424/185.1; 424/204.1

(58) Field of Classification Search
None
See application file for complete search history.

(56) References Cited

U.S. PATENT DOCUMENTS

| | | | |
|---|---|---|---|
| 4,795,740 A | 1/1989 | Cohen et al. | |
| 4,814,432 A | 3/1989 | Freidinger et al. | |
| 5,104,854 A | 4/1992 | Schlesinger et al. | |
| 5,182,265 A | 1/1993 | Bruzzese et al. | |
| 5,260,420 A | 11/1993 | Burnouf-Radosevich et al. | |
| 5,380,727 A | 1/1995 | Deziel et al. | |
| 5,441,936 A | 8/1995 | Houghten et al. | |
| 5,645,849 A | 7/1997 | Pruss et al. | |
| 5,700,780 A | 12/1997 | Beaulieu et al. | |
| 5,807,746 A | 9/1998 | Lin et al. | |
| 5,877,282 A | 3/1999 | Nadler et al. | |
| 6,635,248 B1 | 10/2003 | Ternynck et al. | |
| 7,371,809 B2 | 5/2008 | Brandt et al. | |
| 7,432,045 B2 | 10/2008 | Brandt et al. | |
| 2005/0203024 A1 | 9/2005 | Brandt et al. | |

FOREIGN PATENT DOCUMENTS

| | | |
|---|---|---|
| EP | 0531080 A2 | 3/1993 |
| JP | 4021635 A | 1/1992 |
| WO | 9804717 A2 | 2/1998 |
| WO | 9905302 A1 | 2/1999 |
| WO | 9964449 A2 | 12/1999 |

OTHER PUBLICATIONS

Richards et al., Journal of Virology, 2003, 77(12):6692-6699.*
Walker et al., "AIDS: Escape from the Immune System" Nature, 407:313-314 (2000).
Barouch et al., "Eventual AIDS vaccine failure in a rhesus monkey by viral escape from cytotoxic T lymphocytes" Nature, 415:335-339 (2002).
Desrosiers, "Prospects for an AIDS vaccine" Nature Medicine, 10(3):221-223 (2004).
Feinberg et al., "AIDS vaccine models: Challenging challenge viruses" Nature Medicine, 8(3):207-210 (2002).
Richards et al., "Protection against Recurrent Ocular Herpes Simplex Virus Type 1 Disease after Therapeutic Vaccination of Latently Infected Mice" Journal of Virology, 77(12):6692-6699 (2003).
National Center for Infectious Diseases, Cytomegalovirus Infection (CMV), www.cdc.gov/ncidod/diseases/cmv/htm website last updated Sep. 12, 2005, printout pp. 1-5.
Wagner et al., "Mercaptopurin-Protein-Azokonjugate" Pharmazie, 32(3):157-162 (1977).
Srinivas et al., "Antiviral effects of apolipoprotein A-1 and its synthetic amphipathic peptide analogs" Virology, 176 (1):48-57 (1990).
Srinivas et al., "Membrane interactions of synthetic peptides corresponding to amphipathic helical segments of the human immunodeficiency virus type-1 envelope glycoprotein" Journal of Biological Chemistry, 267(10):7121-7127 (1992).
Wild et al., "A synthetic peptide inhibitor of human immunodeficiency virus replication: correlation between solution structure and viral inhibition" PNAS, 89(21):10537-10541 (1992).
Derossi et al., "The third helix of the Antennapedia homeodomain translocates through biological membranes" Journal of Biological Chemistry, 269(14):10444-10450 (1994).
Wild et al., "Peptides corresponding to a predictive alpha-helical domain of human immunodeficiency virus type 1 gp41 are potent inhibitors of virus infection" PNAS, 91(21):9770-9774 (1994).
Wild et al., "Propensity for a leucine zipper-like domain of human immunodeficiency virus type 1 gp41 to form oligomers correlates with a role in virus-induced fusion rather than assembly of the glycoprotein complex" PNAS, 91 (26):12676-12680 (1994).
Oehlke et al., "Utilization of endothelial cell monolayers of low tightness for estimation of transcellular transport characteristics of hydrophilic compounds" European Journal of Pharmaceutical Sciences, 2(5-6):365-372 (1994).
Lin et al., "Inhibition of nuclear translocation of transcription factor NF-kB by a synthetic peptide containing a cell membrane-permeable motif and nuclear localization sequence" Journal of Biological Chemistry, 270(24):14255-14258 (1995).
Brugidou et al., "The Retro-inverso form of a homeobox-derived short peptide is rapidly internalized by cultured neurons: a new basis for an efficient intracellular delivery system" Biochemical and Biophysical Research Communications, 214(2):685-693 (1995).
Derossi, "Antennapedia homeodomain third helix as a peptide and oligonucleotide vector" Restorative Neurology and Neuroscience, 8(1-2):17-18 (1995).
Rothemund et al., "Recognition of alpha-helical peptide structures using high-performance liquid chromatographic retention data for D-amino acid analogues: Influence of peptide amphipathicity and of stationary phase hydrophobicity" Journal of Chromatography, 689(2):219-226 (1995).

(Continued)

*Primary Examiner* — Stacy B. Chen
(74) *Attorney, Agent, or Firm* — Armstrong Teasdale LLP

(57) ABSTRACT

This invention relates to peptides having antiviral properties. The antiviral peptides comprise membrane transiting peptides, and active fragments and derivatives of such peptides. The antiviral peptides exhibit activity against a broad spectrum of viruses, including enveloped and nonenveloped viruses, and are used in pharmaceutical compositions to prevent and/or treat viral infections.

7 Claims, 11 Drawing Sheets

(56) References Cited

OTHER PUBLICATIONS

Brandt et al., "Evaluation of a peptidomimetic ribonucleotide reductase inhibitor with a murine model of herpes simplex virus virus type 1 ocular disease" Antimicrobial Agents and Chemotherapy, 40(5):1078-1084 (1996).

Derossi et al., "Cell internalization of the third helix of the antennapedia homeodomain is receptor-independent" Journal of Biological Chemistry, 271(30):18188-18193 (1996).

Krause et al., "Conformation of a water-soluble beta-sheet model peptide: A circular dichroism and fourier-transform infrared spectroscopic study of double d-amino acid replacements" International Journal of Peptide & Protein Research, 48(6):559-568 (1996).

Oehlke et al., "Nonendocytic, amphipathicity dependent cellular uptake of helical model peptides" Protein and Peptide Letters, 3(6):393-398 (1996).

Yao et al., "Peptides corresponding to the heptad repeat sequence of human parainfluenza virus fusion protein are potent inhibitors of virus infection" Virology, 223(1):103-112 (1996).

Elliott et al., "Intercellular trafficking and protein delivery by a herpesvirus structural protein" Cell, 88:223-233 (1997).

Yang et al., "Analysis of the murine leukemia virus R peptide: Delineation of the molecular determinants which are important for its fusion inhibition activity" Journal of Virology, 71(11):8490-8496 (1997).

Oehlke et al., "Extensive cellular uptake into endothelial cells of an amphipathic beta-sheet forming peptide" Federation of European Biochemical Societies Letter, 415(2):196-199 (1997).

Rimsky et al., "Determinants of human immunodeficiency virus type 1 resistance to gp41-derived inhibitory peptides" Journal of Virology, 72(2):986-993 (1998).

Rojas et al., "Genetic engineering of proteins with cell membrane permeability" Nature Biotechnology, 16:370-375 (1998).

Phelan et al., "Intercellular delivery of functional p53 by the herpesvirus protein VP22" Nature Biotechnology, 16:440-443 (1998).

Hong et al., "Identification and characterization of novel antimicrobial decapeptides generated by combinatorial chemistry" Antimicrobial Agents and Chemotherapy, 42(10):2534-2541 (1998).

Kilby et al., "Potent suppression of HIV-1 replication in humans by T-20, a peptide inhibitor of gp41-mediated virus entry" Nature Medicine, 4:1302-1307 (1998).

Aldrian-Herrada et al., "A peptide nucleic acid (PNA) is more rapidly internalized in cultured neurons when coupled to a retro-inverso delivery peptide. The antisense activity depresses the target mRNA and protein in magnocellular oxytocin neurons" Nucleic Acids Research, 26(21):4910-4916 (1998).

Bottcher et al., "Peptides that block hepatitis B virus assembly: Analysis by cryomicroscopy, mutagenesis and transfection" EMBO Journal, 17(23):6839-6845 (1998).

Du et al., "Conformational and topological requirements of cell-permeable peptide function" Journal of Peptide Research, 51(3):235-243 (1998).

O'Brien et al., "Anti-human immunodeficiency virus type 1 activity of an oligocationic compound mediated via gp120 V3 interactions" Journal of Virology, 70(5):2825-2831 (1996).

Choudhury et al., "Inhibition of HIV-1 replication by a Tat RNA-binding domain peptide analog" Journal of Acquired Immune Deficiency Syndromes and Human Retrovirology, 17(2):104-111 (1998).

Pooga et al., "Cell penetration by transportan" FASEB Journal, 12(1):67-77 (1998).

Oehlke et al., "Cellular uptake of an alpha-helical amphipathic model peptide with the potential to deliver polar compounds into the cell interior non-endocytically" Biochimica et Biophysica Acta, 1414(1):127-139 (1998).

Zhang et al., "Preparation of functionally active cell-permeable peptides by single-step ligation of two peptide modules" PNAS, 95(16):9184-9189 (1998).

Janek et al., "Water-soluble beta-sheet models which self-assemble into fibrillar structures" Biochemistry, 38(26):8246-8252 (1999).

Brandt et al., "Inhibition of HSV ocular infection by membrane transiting peptides" Investigative Ophthalmology and Visual Science, 42(4):5108 (2000).

T. Boulikas, "Nuclear localization signals (NLS)" Critical Reviews in Eukaryotic Gene Expression, 3(3):193-227 (1993).

Rhoads et al., "Alanine enhances jejunal sodium absorption in the presence of glucose: Studies in piglet viral diarrhea" Pediatric Research, 20(9):879-883 (1986).

Non-Final Office action issued in analogous U.S. Appl. No. 09/777,560 dated Jun. 8, 2007.

Examiner Interview Summary issued in analogous U.S. Appl. No. 09/777,560 dated Mar. 19, 2007.

Final Office action issued in analogous U.S. Appl. No. 09/777,560 dated Oct. 18, 2006.

Non-final Office action issued in analogous U.S. Appl. No. 09/777,560 dated Nov. 7, 2005.

Examiner Interview Summary issued in analogous U.S. Appl. No. 09/777,560 dated Dec. 20, 2006.

Office action from U.S. Appl. No. 12/291,325, dated Apr. 7, 2010.

Office action from U.S. Appl. No. 12/291,325, dated Aug. 31, 2010.

U.S. Appl. No. 12/061,378, filed Apr. 2, 2008.

U.S. Appl. No. 60/184,057, filed Feb. 22, 2000.

U.S. Appl. No. 60/180,823, filed Feb. 7, 2000.

Brandt et al., "A Murine Model of Herpes Simplex Virus-Induced Ocular Disease for Antiviral Drug Testing" Journal of Virological Methods, 36(3):209-222 (1992).

Banfield et al., "Evidence for an interaction of herpes simplex virus with chondroitin sulfate proteoglycans during infection" Virology, 208(2):531-539 (1995).

Berkowitz et al., "Magainins: A new family of membrane-active host defense peptides" Biochemical Pharmacology, 39(4):625-629 (1990).

Cai et al., "Role of glycoprotein B of herpes simplex virus type 1 in viral entry and cell fusion" Journal of Virology, 62(8):2596-2604 (1988).

Campadelli-Fiume et al., "Glycoprotein C-dependent attachment of herpes simplex virus to susceptible cells leading to productive infection" Virology, 178(1):213-222 (1990).

Chou et al., "Prediction of the secondary structure of proteins from their amino acid sequence" Advances in Enzymology and Related Areas of Molecular Biology, 47:45-147 (1978).

Cockrell et al., "Herpes Simplex Virus 2 UL45 Is a Type II Membrane Protein" Journal of Virology, 72(5):4430-4433 (1998).

Coen et al., "Fine mapping and molecular cloning of mutations in the herpes simplex virus DNA polymerase locus" Journal of Virology, 49(1):236-247 (1984).

Cohen et al., "Specific inhibition of herpesvirus ribonucleotide reductase by a nonapeptide derived from the carboxy terminus of subunit 2" Nature, 321(6068):441-443 (1986).

Desai et al., "Excretion of Non-infectious Virus Particles Lacking Glycoprotein H by a Temperature-sensitive Mutant of Herpes Simplex Virus Type 1: Evidence that gH Is Essential for Virion Infectivity" Journal of General Virology, 69:1147-1156 (1988).

Dutia et al., "Specific inhibition of herpesvirus ribonucleotide reductase by synthetic peptides" Nature, 321(6068):439-441 (1986).

Fawell et al., "Tat-mediated delivery of heterologous proteins into cells" PNAS, 91(2):664-668 (1994).

Fields et al., "HBTU activation for automated Fmoc solid-phase peptide synthesis" Peptide Research, 4(2):95-101 (1991).

Fuller et al., "Anti-glycoprotein D antibodies that permit adsorption but block infection by herpes simplex virus 1 prevent virion-cell fusion at the cell surface" PNAS, 84(15):5454-5458 (1987).

Fuller et al., "Herpes simplex virus type 1 entry through a cascade of virus-cell interactions requires different roles of gD and gH in penetration" Journal of Virology, 66(8):5002-5012 (1992).

Gennaro et al., "Remington's Pharmaceutical Sciences", 18th ed., Mack Publishing Company, Easton, Pennsylvania (1990).

Geraghty et al., "Entry of Alphaherpesviruses Mediated by Poliovirus Receptor Related Protein I and Poliovirus Receptor" Science, 280(5369):1618-1620 (1998).

Gibbs et al., "Sequence and mapping analyses of the herpes simplex virus DNA polymerase gene predict a C-terminal substrate binding domain" PNAS, 82(23):7969-7973 (1985).

(56) References Cited

OTHER PUBLICATIONS

Grau et al., "Herpes Simplex Virus Stromal Keratitis Is Not Titer-Dependent and Does Not Correlate with Neurovirulence" Investigative Ophthalmology and Visual Science, 30:2474-2780 (1989).
Gross et al., "The Peptides: Analysis, Synthesis, Biology" vol. 1-8, Academic Press, New York, New York (1979-1987).
Haanes et al., "The UL45 gene product is required for herpes simplex virus type 1 glycoprotein B-induced fusion" Journal of Virology, 68(9):5825-5834 (1994).
Hall et al., "Aphidicolin resistance in herpes simplex virus type 1 appears to alter substrate specificity in the DNA polymerase" Journal of Virology, 63(6):2874-2876 (1989).
Handler et al., "Cross-linking of glycoprotein oligomers during herpes simplex virus type 1 entry" Journal of Virolgy, 70(9):6076-6082 (1996).
Herold et al., "Glycoprotein C of herpes simplex virus type 1 plays a principal role in the adsorption of virus to cells and in infectivity" Journal of Virology, 65(3):1090-1098 (1991).
Herold et al., "Glycoprotein C-independent binding of herpes simplex virus to cells requires cell surface heparan sulphate and glycoprotein B" Journal of General Virology 75:1211-1222 (1994).
Herold et al., "Differences in the susceptibility of herpes simplex virus types 1 and 2 to modified heparin compounds suggest serotype differences in viral entry" Journal of Virology, 70(6):3461-3469 (1996).
Hutchinson et al., "A novel herpes simplex virus glycoprotein, gL, forms a complex with glycoprotein H (gH) and affects normal folding and surface expression of gH" Journal of Virology, 66(4):2240-2250 (1992).
Highlander et al., "Neutralizing monoclonal antibodies specific for herpes simplex virus glycoprotein D inhibit virus penetration", Journal of Virology, 61(11):3356-3364 (1987).
Johnson et al., "Herpes simplex virus glycoprotein D mediates interference with herpes simplex virus infection" Journal of Virology, 63(2):819-827 (1989).
C. W. Knopf, "The Herpes Simplex Virus Type 1 DNA Polymerase Gene: Site of Phosphonoacetic Acid Resistance Mutation in Strain Angelotti is Highly Conserved" Journal of General Virology, 68:1429-1433 (1987).
Krummenacher et al., "Herpes Simplex Virus Glycoprotein D Can Bind to Poliovirus Receptor-Related Protein 1 or Herpesvirus Entry Mediator, Two Structurally Unrelated Mediators of Virus Entry" Journal of Virology, 72(9):7064-7074 (1998).
Laquerre et al., "Heparan Sulfate Proteoglycan Binding by Herpes Simplex Virus Type 1 Glycoproteins B and C,.Which Differ in Their Contributions to Virus Attachment, Penetration, and Cell-to-Cell Spread" Journal of Virology, 72 (7):6119-6130 (1998).
Ligas et al., "A herpes simplex virus mutant in which glycoprotein D sequences are replaced by beta-galactosidase sequences binds to but is unable to penetrate into cells" Journal of Virology, 62(5):1486-1494 (1988).
Lycke et al., "Binding of Herpes Simplex Virus to Cellular Heparan Sulfate, an initial Step in the Adsorption Process" Journal of General Virology, 72:1131-1137 (1991).
Lehninger et al., "Principles of Biochemistry", p. 113, Worth Publishers, New York, New York (1983).
Manservigi et al., "Cell fusion induced by herpes simplex virus is promoted and suppressed by different viral glycoproteins" PNAS, 74(9): 3913-3917 (1977).
Matthews et al., "The structure and function of the HSV DNA replication proteins: Defining novel antiviral targets" Antiviral Research, 20(2):89-114 (1993).
Merrifield et al., "Solid Phase Peptide Synthesis I. The synthesis of a tetrapeptide.", Journal of the American Chemical Society, 85:2149-2154 (1963).
Meienhofer et al., "Solid Phase Synthesis Without Repetitive Acidolysis: Preparation of Leucyl-alanyl-glycyl-valine Using 9-Fluorenylmethyloxycarbonylamino Acids" International Journal of Peptide and Protein Research, 13(1):35-42 (1979).

Minson et al., "An Analysis of the Biological Properties of Monoclonal Antibodies against Glycoprotein D of Herpes Simplex Virus and Identification of Amino Acid Substitutions that Confer Resistance to Neutralization" Journal of General Virology, 67:1001-1013 (1986).
Montgomery et al., "Herpes simplex virus-1 entry into cells mediated by a novel member of the TNF/NGF receptor family" Cell, 87(3):427-436 (1996).
Nicola et al., "Structure-function analysis of soluble forms of herpes simplex virus glycoprotein D" Journal of Virology, 70(6):3815-3822 (1996).
Nicola et al., "Monoclonal Antibodies to Distinct Sites on Herpes Simplex Virus (HSV) Glycoprotein D Block HSV Binding to HVEM" Journal of Virology, 72(5):3595-3601 (1998).
Nisole et al., "The Anti-HIV Pseudopeptide HB-19 Forms a Complex with the Cell-surface-expressed Nucleolin Independent of Heparan Sulfate Proteoglycans" Journal of Biological Chemistry, 274(39):27875-27884 (1999).
Roop et al., "A mutant herpes simplex virus type 1 unable to express glycoprotein L cannot enter cells, and its particles lack glycoprotein H" Journal of Virology, 67(4): 2285-2297 (1993).
Sasadeusz et al., "Homopolymer mutational hot spots mediate herpes simplex virus resistance to acyclovir" Journal of Virology, 71(5):3872-3878 (1997).
Schroeder et al., "The Peptides", vol. 1., Academic Press, p. 2-128, New York, New York (1965).
Schwarze et al., "In Vivo Protein Transduction: Delivery of a Biologically Active Protein into the Mouse" Science, 285(5433):1569-1572 (1999).
Sears et al., "Infection of polarized MDCK cells with herpes simplex virus 1: Two asymmetrically distributed cell receptors interact with different viral proteins" PNAS, 88(12):5087-5091 (1991).
I. H. Segel, "Biochemical Calculations", 2nd ed., John Wiley and Sons, Inc., New York, New York (1976).
Shieh et al., "Cell surface receptors for herpes simplex virus are heparan sulfate proteoglycans.", The Journal of Cell Biology, 116(5):1273-1281 (1992).
Shieh et al., "Herpes virus-induced cell fusion that is dependent on cell surface heparan sulfate or soluble heparin" Journal of Virology, 68(2): 1224-1228 (1994).
P. G. Spear, "Entry of alphaherpesviruses into cells" Seminars in Virology, 4(3):167-180 (1993).
Stewart et al., "Solid Phase Peptide Synthesis", 2nd Ed., Pierce Chem. Co, Rockford, Illinois (1984).
Tal-Singer et al., "Interaction of herpes simplex virus glycoprotein gC with mammalian cell surface molecules" Journal of Virology, 69(7):4471-4483 (1995).
Theodore et al., "Intraneuronal delivery of protein kinase C pseudosubstrate leads to growth cone collapse" Journal of Neuroscience, 15(11):7158-7167(1995).
Turner et al., "Glycoproteins gB, gD, and gHgL of Herpes Simplex Virus Type 1 Are Necessary and Sufficient to Mediate Membrane Fusion in a Cos Cell Transfection System" Journal of Virology, 72(1):873-875 (1998).
Visalli et al., "The HSV-1 UL45 18 kDa Gene Product Is a True Late Protein and a Component of the Virion" Virus Research, 29(2):167-178 (1993).
Vives et al., "A Truncated HIV-1 Tat Protein Basic Domain Rapidly Translocates through the Plasma Membrane and Accumulates in the Cell Nucleus" Journal of Biology Chemistry, 272(25): 16010-16017 (1997).
Westra et al., "Glycoprotein H of herpes simplex virus type 1 requires glycoprotein L for transport to the surfaces of insect cells" Journal of Virology, 71(3): 2285-2291 (1997).
Whitbeck et al., "Glycoprotein D of herpes simplex virus (HSV) binds directly to HVEM, a member of the tumor necrosis factor receptor superfamily and a mediator of HSV entry" Journal of Virology, 71(8): 6083-6093 (1997).
J. M. White, "Membrane Fusion" Science, 258(5084):917-923 (1992).
R. J. Whitley, "Epidemiology of herpes simplex viruses" B. Roizman Ed., The Herpesviruses, vol. 3, New York, Plenum Press pp. 1-44 (1982).

(56) References Cited

OTHER PUBLICATIONS

Wudunn et al., "Initial interaction of herpes simplex virus with cells is binding to heparan sulfate" Journal of Virology, 63(1):52-58 (1989).

"The 20 Amino Acids: Hydrophobic, Hydrophilic, Polar and Charged Amino Acids and their Function in Protein Structures" available at http://www.proteinstructures/Structure/Structure/amino-acids.html, downloaded Apr. 27, 2012.

* cited by examiner

SEQUENCE LISTING

```
<160> NUMBER OF SEQ ID NOS: 32

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Lys Lys Ala Ala Val Ala Leu Leu Pro Ala Val Leu Leu Ala
1               5                   10                  15

Leu Leu Ala Pro
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Lys Lys Ala Ala Val Ala Leu Leu Pro Ala Val Leu Leu Ala
1               5                   10                  15

Leu Leu Ala Pro
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Lys Lys Ala Ala Val Ala Leu Leu Ala Val Leu Leu Ala Leu
1               5                   10                  15
```

Leu Ala Pro Pro
            20

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Lys Lys Pro Ala Val Leu Leu Ala Leu Leu Ala
 1               5                  10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Leu Ala Leu Lys Leu Ala Leu Lys Ala Leu Lys Ala Ala Leu Lys
 1               5                  10                  15

Leu Ala

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: D-form amino acid

<400> SEQUENCE: 6

Lys Leu Ala Leu Lys Leu Ala Leu Lys Ala Leu Lys Ala Ala Leu Lys
 1               5                  10                  15

Leu Ala

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gln Ile Lys Ile Trp Phe Pro Asn Arg Arg Met Lys Trp Lys Lys
 1               5                  10                  15

Pro Gly Tyr Ala Gly Ala Val Val Asn Asp Leu
            20                  25

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(16)
<223> OTHER INFORMATION: D-form amino acid

<400> SEQUENCE: 8

Arg Gln Ile Lys Ile Trp Phe Pro Asn Arg Arg Met Lys Trp Lys Lys
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Gln Ile Lys Ile Phe Phe Pro Asn Arg Arg Met Lys Phe Lys Lys
 1               5                  10                  15

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Gly Arg Lys Lys Arg Arg Gln Arg Arg Arg Pro Gly Tyr Ala Gly
 1               5                  10                  15

Ala Val Val Asn Asp Leu
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Gly Arg Lys Lys Arg Arg Gln Arg Arg Arg Pro Gly Asp Val Tyr
 1               5                  10                  15

Ala Asn Gly Leu Val Ala
            20

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 13

Asp Pro Lys Gly Asp Pro Lys Gly Val Thr Val Thr Val Thr Val Thr
  1               5                  10                  15

Val Thr Gly Lys Gly Asp Pro Lys Pro Asp
             20                  25

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Formula
      peptide
<220> FEATURE:
<221> NAME/KEY: MOD_RES
<222> LOCATION: (1)..(10)
<223> OTHER INFORMATION: charged amino acid; e.g. Lys or Arg; this
      region may encompass either 0 or 3-10 Xaa repeats with the proviso
      that in one embodiment either residues 1-10 are not present or
      residues 27-36 are not present
<220> FEATURE:
<221> NAME/KEY: MOD_RES
<222> LOCATION: (27)..(36)
<223> OTHER INFORMATION: charged amino acid; e.g. Lys or Arg; this
      region may encompass either 0 or 3-10 Xaa repeats with the proviso
      that in one embodiment either residues 1-10 are not present or
      residues 27-36 are not present

<400> SEQUENCE: 14

Xaa Xaa Xaa Xaa Xaa Xaa Xaa Xaa Xaa Xaa Ala Ala Val Ala Leu Leu
  1               5                  10                  15

Pro Ala Val Leu Leu Ala Leu Leu Ala Pro Xaa Xaa Xaa Xaa Xaa Xaa
             20                  25                  30

Xaa Xaa Xaa Xaa
         35

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Formula
      peptide
<220> FEATURE:
<221> NAME/KEY: MOD_RES
<222> LOCATION: (1)..(10)
<223> OTHER INFORMATION: charged amino acid; e.g. Lys or Arg; this
      region may encompass either 0 or 3-10 Xaa repeats with the proviso
      that in one embodiment either residues 1-10 are not present or
      residues 20-29 are not present
<220> FEATURE:
<221> NAME/KEY: MOD_RES
<222> LOCATION: (20)..(29)
<223> OTHER INFORMATION: charged amino acid; e.g. Lys or Arg; this
      region may encompass either 0 or 3-10 Xaa repeats with the proviso
      that in one embodiment either residues 1-10 are not present or
      residues 20-29 are not present

<400> SEQUENCE: 15

Xaa Xaa Xaa Xaa Xaa Xaa Xaa Xaa Xaa Xaa Pro Ala Val Leu Leu Ala
  1               5                  10                  15

Leu Leu Ala Xaa Xaa Xaa Xaa Xaa Xaa Xaa Xaa Xaa Xaa
             20                  25

<210> SEQ ID NO 16
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Arg Arg Lys Lys
  1

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Lys Lys Leu Ala Ala Leu Pro Leu Val Leu Ala Ala Pro Leu
  1               5                  10                  15

Ala Val Leu Ala
             20

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Lys Lys Ala Ala Val Ala Leu Leu Pro
  1               5                  10

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Lys Lys Ala Val Ala Val Ala Val Pro Ala Val Leu Leu Ala
  1               5                  10                  15

Leu Leu Ala Pro
             20

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Lys Lys Pro Ala Val Leu Leu Ala
  1               5                  10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Arg Arg Lys Lys Pro Ala Val Leu Leu Ala Leu Leu Ala
  1               5                  10

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Lys Lys Pro Ala Val Leu Leu Ala Leu Leu Ala Leu Leu Ala
  1               5                  10                  15

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Arg Lys Lys Ala Leu Leu Pro Ala Val Leu Leu Ala Leu Leu Ala
  1               5                  10                  15

Pro

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Lys Lys Pro Ala Val Leu Leu Ala Leu Leu Ala Pro
  1               5                  10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Lys Lys Leu Leu Ala Leu Leu Ala Pro
  1               5                  10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Lys Lys Leu Leu Ala Pro
  1               5

<210> SEQ ID NO 27
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Lys Lys Ala Ala Val Ala Leu Leu Pro Ala Val Leu Leu Ala
 1               5                  10                  15

Leu

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Lys Lys Ala Ala Val Ala Val Val Pro Ala Val Leu
 1               5                  10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Lys Lys Ala Ala Val Ala Val Val Pro
 1               5                  10

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Lys Lys Ala Ala Val Ala
 1               5

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Gly Tyr Ala Gly Ala Val Val Asn Asp Leu
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 32

Pro Gly Asp Val Tyr Ala Asn Gly Leu Val Ala
  1               5                   10
```

US 8,748,565 B2

PHARMACOLOGICALLY ACTIVE ANTIVIRAL PEPTIDES AND METHODS OF THEIR USE

CROSS-REFERENCE TO RELATED APPLICATIONS

This application is a divisional application of U.S. application Ser. No. 09/777,560, filed Feb. 6, 2001, now U.S. Pat. No. 7,371,809, which claims priority to U.S. Provisional Patent Application Nos. 60/184,057, filed Feb. 2, 2000 and 60/180,823, filed Feb. 7, 2000, the entire contents of which are hereby incorporated by reference.

GOVERNMENT SUPPORT

Statement as to Rights to Inventions Made Under Federally-Sponsored Research and Development This invention was made with United States Government support awarded by the following agency: DOD ARPA Grant No. MDA972-97-1-0005. The United States Government has certain rights in this invention.

FIELD OF THE INVENTION

This invention relates to peptides having antiviral properties. More specifically, the invention relates to peptides exhibiting activity against a broad spectrum of viruses, to pharmaceutical compositions comprising the peptides, and to methods of using the peptides to prevent and/or treat viral infections.

BACKGROUND OF THE INVENTION

In recent years, various groups of peptide derivatives having activity against viruses have been disclosed. Examples of these peptides are disclosed in U.S. Pat. No. 5,700,780, issued to Beaulieu et al.; U.S. Pat. No. 5,104,854, issued to Schlesinger et al.; U.S. Pat. No. 4,814,432 issued to Freidinger et al.; Dutia et al., Nature 321:439 (1986); and Cohen et al., Nature 321:441 (1986). However, many of the known antiviral peptides known in the art are extremely hydrophobic, and therefore, not very bioavailable. Moreover, many of these known antiviral peptides show activity against only a few types of viruses, due to their particular mechanisms of action. Additionally, many of these synthetic peptides are not effective in preventing initial viral infection, or are not functional when applied topically.

One of the most successful nucleoside analogs developed as an antiviral agent to-date is acyclovir. Acyclovir is a synthetic purine nucleoside analog with in vitro and in vivo inhibitory activity against herpes simplex virus type I (HSV-1), herpes simplex virus type II (HSV-2), and varicella zoster virus (VZV). In cell culture, acyclovir's highest antiviral activity is against HSV-1, followed in decreasing order of potency against HSV-2 and VZV. However, the use of acyclovir may be contraindicated. Moreover, some herpes simplex viruses have become resistant to acyclovir.

Recently, there has been considerable research into antiviral compounds that could be incorporated into topical virucides and condom lubricants to help stem the spread of human immunodeficiency virus (HIV). The need for such a product is high; the appropriate antiviral and/or virucidal compound that prevents HIV infection would be of great use in both developed and undeveloped nations.

Therefore, there remains a need for antivirals which exhibit a high activity against a broad spectrum of viruses. There also remains a need for antivirals that can be applied topically, and are effective at preventing viral infection.

DETAILED DESCRIPTION OF THE INVENTION

Figures 1A, 1B:
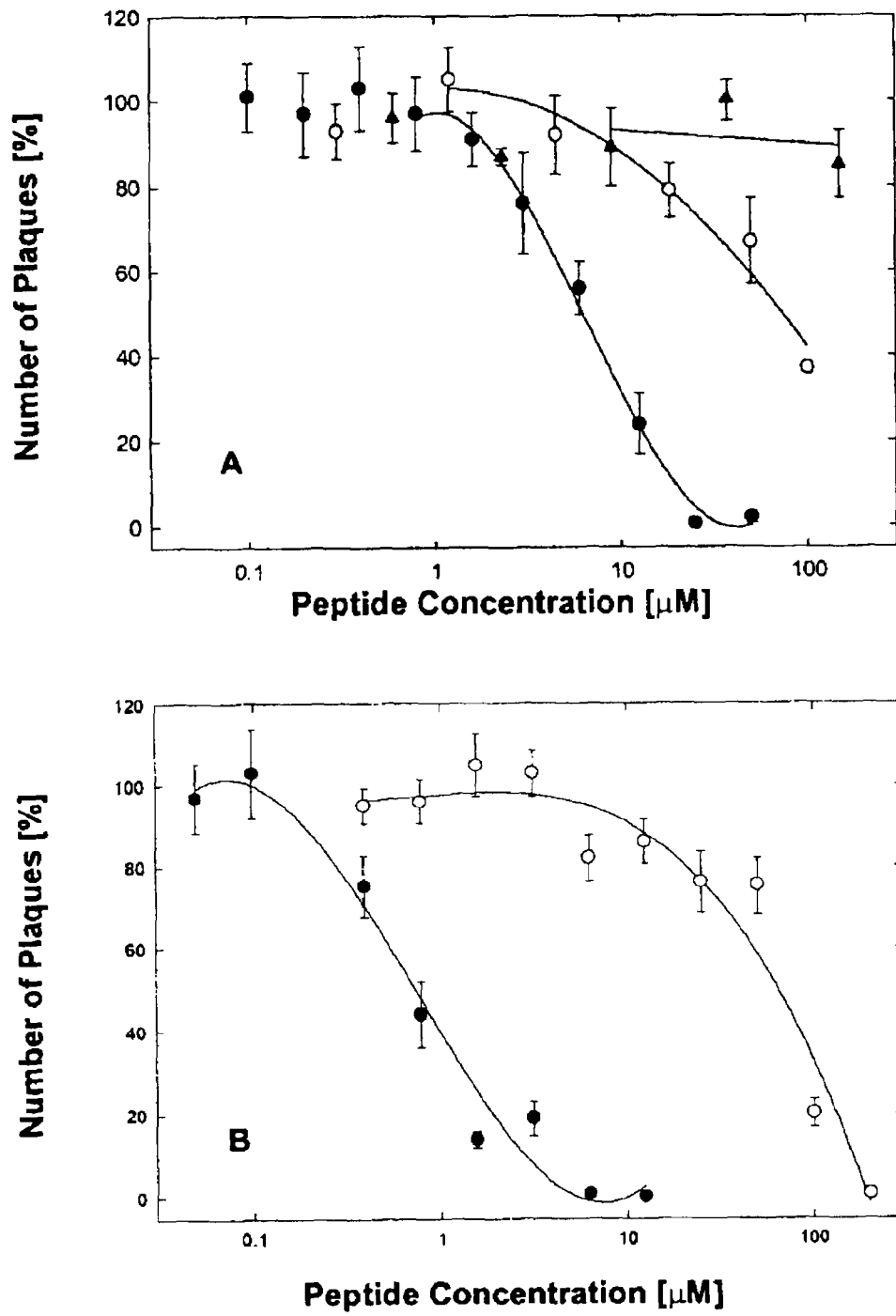
FIGS. 1A, 1B, 1D, and FIG. 1E are graphical representations showing the dose-dependent inhibition of HSV-1 by an antiviral peptides of the present invention (SEQ ID NO:1), (SEQ ID NO:3) and (SEQ ID NO:4) compared to control peptides (SEQ ID NO:16 and SEQ ID NO:17).

In the description that follows, a number of terms are utilized extensively. Definitions are herein provided to facilitate understanding of the invention.

Antiviral peptide: The antiviral peptide comprises at least in part a membrane transiting peptide, or a fragment or a derivative thereof, that is a pharmacologically effective antiviral agent when administered in an effective amount.

Effective amount: A predetermined amount of the antiviral peptide, i.e., an amount of the peptide sufficient to be effective against the viral organisms in vivo or topically for treatment or prophylactic effect.

Membrane transiting peptide (membrane transiting motif): A peptide having a sequence of amino acids that render the peptide capable of traversing lipid bilayer membranes to enter cells or subcellular compartments.

Pharmaceutically acceptable carrier: An acceptable cosmetic vehicle for administering antiviral peptides to mammals comprising one or more non-toxic excipients which do not react with or reduce the effectiveness of the pharmacologically active antiviral peptide contained therein.

Solubility tag: a short peptide sequence comprised of charged amino acids which, when attached to a terminal residue of a longer insoluble peptide sequence, will improve solubility in an aqueous medium.

In this application, the standard one letter abbreviated names for the amino acids are used throughout. See Lehninger et al. "Principles of Biochemistry", Worth Publishers (New York, N.Y.) p. 113 (1983). All amino acid sequences in this application are depicted using standard nomenclature, with the left most amino acid residue at the end of each sequence being the amino-terminal residue and the residue at the right end of each sequence being the carboxyl-terminal residue. The amino acids of the peptides described herein may be either levo amino acids or dextro amino acids, as denoted 1 or d before the peptide sequence (See Table 1).

The present invention relates to novel antiviral peptides which are based on membrane transiting peptides. Various membrane transiting peptides are well known in the art. It has been surprisingly and unexpectedly discovered that membrane transiting peptides exhibit a broad spectrum of antiviral activity, including such activity when applied topically or administered in vivo. Exemplary antiviral peptides of the present invention derived from membrane transiting peptides are described below Table 1, although any membrane transiting peptide known in the art may be used, see, e.g., Pooga et al., *FASEB J.*, 12:67 (1998) and Oehlke et al., *FEBS Lett.*, 415:196 (1997).

As shown in Table 1, SEQ ID NOS: 1-4 have had a solubility tag covalently attached. The present invention relates to such novel antiviral peptides which in part comprise a solubility tag covalently attached and have the following sequence: $(X1)_n$-A-A-V-A-L-L-P-A-V-L-L-A-L-L-A-P-$(X2)_m$ (SEQ ID NO:14) or $(X1)_n$-P-A-V-L-L-A-L-L-A-$(X2)_m$ (SEQ ID NO:15) wherein X1 and X2 are selected from one or more charged amino acid residues (e.g. K, R) where each X1 and each X2 may be the same or different charged amino acid residue; and wherein n has a value of 0 or 3-10, and m has a value of 0 or 3-10, wherein in one embodiment either m=0 or n=0. One example of a solubility tag is R-R-K-K (SEQ ID NO:16). In the preferred embodiment, all charged amino acid residues of the solubility tag are positively charged amino acid residues. The inventors have surprising and unexpectedly discovered that insoluble membrane transiting peptides, when coupled to a solubility tag, create antiviral peptides that exhibit strong antiviral activity against a broad spectrum of viruses.

Many membrane transiting peptides may function as antiviral peptides of the present invention without the need for solubility tags. See Table 1. Moreover, although solubility tags may improve the solubility of some membrane transiting

TABLE 1

Antiviral Peptides

| Peptide | SEQUENCE ID NUMBER | Sequence |
|---|---|---|
| EB | SEQ ID NO:1 | $NH_2$- RRKKAAVALLPAVLLALLAP-COOH |
| bEB | SEQ ID NO:2 | b - RRKKAAVALLPAVLLALLAP-COOH |
| EBPP | SEQ ID NO:3 | $NH_2$- RRKKAAVALLAVLLALLAPP-COOH |
| LALA | SEQ ID NO:4 | $NH_2$- RRKKPAVLLALLA-COOH |
| bKLA | SEQ ID NO:5 | b - KLALKLALKALKAALKLA-amide |
| bKLAd$_{11,12}$ | SEQ ID NO:6 | b - KLALKLALKALKAALKLA-amide |
| bHOM-9 | SEQ ID NO:7 | b - RQIKIWFPNRRMKWKK-9 |
| bHOMd | SEQ ID NO:8 | b - RQIKIWFPNRRMKWKK-amide |
| bHOMFF | SEQ ID NO:9 | b - RQIKIFFPNRRMKFKK-amide |
| bTAT-9 | SEQ ID NO:10 | b - YGRKKRRQRRR-9 |
| bTAT-9x | SEQ ID NO:11 | b - YGRKKRRQRRR-9x |
| N$^{E13}$-biotinyl transportan | SEQ ID NO:12 | GWTLNSAGYLLGKINLKALAALAKKIL<br>\|<br>b |
| VT5 | SEQ ID NO:13 | fluor-DPKGDPKGVTVTVTVTVTGKGDPKPD |

Residues indicated in bold are positively charged residues
b = biotin-aminohexanoyl
d = peptide composed of all D amino acid residues
fluor = fluorescent label
-9 = PGYAGAVVNDL-COOH
-9x = PGDVYANGLVA-COOH The antiviral peptides of the present invention may be used alone in an effective amount. Although most membrane transiting peptides are soluble, some are not, although insoluble membrane transiting motifs may be utilized in antiviral peptides by the following method. If the antiviral peptide is insoluble in an aqueous pharmaceutically acceptable carrier, a solubility tag may be added to the antiviral peptide.

peptides, these particular membrane transiting peptides may be suitable as antiviral peptides without incorporating solubility tags.

The antiviral peptides of the present invention may have various reactive tags attached to their terminal amino acid residues. Such tags may be useful in detection/removal of the synthetic peptides of the present invention. Such tags may include, by way of example only, biotin, as well as any other tags well-known in the art. SEQ ID NOS: 2, 5-12 and Example 2 demonstrate the inclusion of such reactive tags.

Derivatives and fragments of membrane transiting peptides of the present have also been found to be useful as antiviral peptides. The present invention relates to novel antiviral peptides comprised a membrane transiting motif wherein one or more of the amino acid residues of the membrane transiting motif are deleted or substituted for other amino acid residues. Such substituted or fragment membrane transiting motifs must retain antiviral activity. The antiviral peptides according to the present invention comprising a substituted membrane transiting motif or fragment thereof can be tested for antiviral activity via the methodology described in the following Examples. Example 2 demonstrates that antiviral peptides comprising substituted membrane transiting motifs retain antiviral activity, as shown by SEQ ID NO:3, described in Table 1. This derivative differs from SEQ ID NO:1 only in that both proline amino acid residues have been placed at the carboxy terminus of the peptide. Table 2 lists potential active fragments of an antiviral peptide according to the present invention.

2-128 (1965); "The Peptides: Analysis, Synthesis, Biology", (E. Gross et al., Eds.), Academic Press, New York, N.Y., Vol. 1-8, (1979-1987); Stewart and Young, in "Solid Phase Peptide Synthesis", 2nd Ed., Pierce Chem. Co., Rockford, Ill. (1984); Wild et al. *Proc. Natl. Acad. Sci. USA,* 89: 10537 (1992); and Rimsky et al., *J. Virol,* 72: 986 (1998).

As demonstrated in the following Examples, the antiviral peptides of the present invention show antiviral activity against a wide range of enveloped and nonenveloped viruses. Examples of such enveloped viruses include, but are not limited to, human immunodeficiency virus (HIV), vesiculovirus (VSV), herpes simplex viruses (HSV-1 and HSV-2), and other herpes viruses, for example, varicella-zoster virus (VZV), EBV, equine herpes virus (EHV), and human cytomegalovirus (HCMV). Examples of nonenveloped viruses include, but are not limited to, human papilloma virus (HPV) and adenoviruses.

A method for demonstrating the inhibitory effect of the antiviral peptides of the present invention on viral replication is the well-known cell culture technique as taught in the following Examples. Such methods are well known in the art. See Wild et al., *Proc. Natl. Acad. Sci. USA,* 89: 10537 (1992).

TABLE 2

Potential Active Fragments of Antiviral Peptides

| Peptide | Sequence | Purpose |
| --- | --- | --- |
| P11 (SEQ ID NO: 18) | RRKKAAVALLP | activity of n-terminal |
| P12 (SEQ ID NO: 19) | RRKKAVAVAVPAVLLALLAP | half spacing of LLA motif |
| Peptides testing role of LLA motif | | |
| P13 (SEQ ID NO: 20) | RRKKPAVLLA | One LLA |
| P14 (SEQ ID NO: 21) | RRKKPAVLLALLA | Two LLAs |
| P15 (SEQ ID NO: 22) | RRKKPAVLLALLALLA | Three LLAs |
| Peptides for testing sequential removal of aa triplets | | |
| P16 (SEQ ID NO: 23) | RRKKALLPAVLLALLAP | -3N-terminus |
| P17 (SEQ ID NO: 24) | RRKKPAVLLALLAP | -6N-terminus |
| P18 (SEQ ID NO: 25) | RRKKLLALLAP | -9N-teminus |
| P19 (SEQ ID NO: 26) | RRKKLLAP | -12N-terminus |
| P20 (SEQ ID NO: 27) | RRKKAAVALLPAVLLAL | -3C-terminus |
| P21 (SEQ ID NO: 28) | RRKKAAVAVVPAVL | -6C-terminus |
| P22 (SEQ ID NO: 29) | RRKKAAVAVVP | -9C-terminus |
| P23 (SEQ ID NO: 30) | RRKKAAVA | -12C-terminus |

Such derivatives and fragments are within the scope of the present invention.

The peptides of the present invention can be prepared by processes which incorporate methods commonly used in peptide synthesis such as classical solution coupling of amino acid residues and/or peptide fragments, and, if desired, solid phase techniques. Such methods are described in the following Examples. Any method for peptide synthesis well known in the art may be used, for example, Schroeder and Lubke, in "The Peptides", Vol. 1, Academic Press, New York, N.Y., pp.

The therapeutic efficacy of the antiviral peptides as antiviral agents can be demonstrated in laboratory animals, for example, by using a murine model as shown in Example 10.

Additionally, the therapeutic effect of the pharmacologically active peptides of the present invention can be shown in humans via techniques well-known in the art. See, for example, Kilby et al., *Nature Medicine* 4: 1302 (1998).

An antiviral peptide of the present invention would be employed as an antiviral agent by administering the peptide topically to a warm-blooded animal, e.g., humans, horses, other mammals, etc. The peptide may be administered in an vehicle comprising one or more pharmaceutically acceptable carriers, the proportion of which is determined by the solubility in chemical nature of the peptide, chosen route of administration and standard biological administration. Suitable vehicles or carriers for the formulations of the peptide are described in the standard pharmaceutical texts. See "Remington's Pharmaceutical Sciences", 18$^{th}$ Ed., Mack Publishing Company, Easton, Pa. (1990).

For topical administration, the antiviral peptide can be formulated in a pharmaceutically accepted vehicle containing an effective amount of the antiviral peptide, typically 0.1 to 10%, preferably 5%, of the antiviral peptide. Such formulations can be in the form of a solution, cream or lotion. The antiviral peptides of the present invention may also be used for treating viral infections of the skin or part of the oral or genital cavity. The antiviral peptides can be used individually or in combination, to treat a wider variety of viruses. Such topical applications could be applied to barrier materials to protect the wearer, such as gloves, condoms and other barriers known in the art.

For systemic administration, the antiviral peptides of the present invention may be administered by either intravenous, subcutaneous, or intramuscular injection, alone or in compositions with pharmaceutically accepted vehicles or carriers. For administration by injection, it is preferred to use the antiviral peptide in a solution in a sterile aqueous vehicle which may also contain other solutes such as buffers or preservatives as well as sufficient quantities of pharmaceutically acceptable salts or of glucose to make the solution isotonic. The antiviral peptides of the present invention can be obtained in the form of therapeutically acceptable salts that are well-known in the art.

The dosage of the antiviral peptides of the present invention will vary with the form of administration and depend upon the particular antiviral peptide(s) chosen for the combination. Furthermore, it will vary with the particular host under treatment. In general, the antiviral peptides are most desirably administered at a concentration level that will generally afford antiviral effective results against the selected virus(es) without causing any harmful or deleterious side effects.

The present invention is further described with reference to the following illustrated Examples. Unless defined otherwise, all technical and scientific terms used herein have the same meaning as commonly illustrated by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies well-known to one of ordinary skill in the art. The materials, methods and Examples are illustrative only and not limiting. All references cited herein are incorporated by reference.

Example 1

Protocols and Materials

Cell Culture and Virus:
The procedures for growing Vero cells and preparing high titer stocks of HSV-1 KOS as described in (Grau et al., *Invest. Ophthal. and Vis. Sci.* 30: 2474 (1989)) were utilized. Vero cells were maintained in carbonate-buffered DMEM supplemented with 5% calf serum and 5% fetal bovine serum (regular medium). For some studies, cells were switched to serum-free DMEM buffered with 25 mM Hepes (pH 7.4) and allowed to adapt to that medium for 30 min prior to experimental treatments. Vero cells were seeded into wells (0.28 cm$^2$) of microtiter plates either at $3.5 \times 10^4$ cells/well for use 1 day later ($8 \times 10^4$ cells/well) or at $1 \times 10^4$ cells/well for use 3 days later ($2 \times 10^5$ cells/well).

Plaque Reduction Assay:
Confluent Vero cell cultures in microtiter plates were infected for 1 hour at 37° C. in 40 μl of medium. Except where indicated, peptide treatments in 40 μl of medium lasted from 1 hour before through 1 hour after infection. At the end of the adsorption period, the cultures were re-fed with 100 μl of regular medium. Plaque formation was scored 2 days later and the number of plaques scored per well was normalized to the number counted in the absence of peptide. Using an ocular micrometer, plaque size ($\pi/2 \times L \times S$) was determined by measuring the largest plaque diameter (L) and the diameter at a 90° angle to that (S). The size of each of the first 40 scored plaques was measured except when a plaque included less than 10 rounded cells or touched the side of the well.

Yield Reduction Assay:
Three days post-infection, Vero cell cultures in microtiter plates were frozen (−80° C.) and thawed (37° C.) three times. Cells were suspended by repeated pipetting and microtiter plates were spun for 10 min at 700×g in a Beckman model TJ-6 tabletop centrifuge. The virus-containing supernates were serially diluted in regular medium and titered on Vero cells. Plaques were counted after staining the monolayers with crystal violet as taught by Grau et al., *Invest. Ophthalmol. Vis. Sci.* 30:2474 (1989).

Attachment Assay:
HSV-1 KOS was labeled with [$^{32}$P]-orthophosphate to a specific activity of 0.01 cpm/pfu. Briefly, Vero cells were infected at a moi of 5.0 and at 6 hours post-infection, [$^{32}$P]-orthophosphate (0.5 mCi/ml) was added. At 18 hours post-infection, the cells and culture medium were harvested separately. The cells were subjected to 3 freeze-thaw cycles and cell debris was pelleted by centrifugation at 2000×g for 10 min. The freeze-thaw supernatant was combined with the media and virus was pelleted by centrifugation through a 26% sucrose gradient cushion as taught by Visalli et al., *Virus Res.* 29:167 (1993). The viral pellet was resuspended in PBS for use. Confluent Vero cell cultures in microtiter plates were switched to serum-free DMEM, chilled on ice, and maintained at 4° C. After 30 min, peptides were added and 60 min later, cells were incubated for 2 hours with $^{32}$P-virus ($2 \times 10^4$ cpm/well). After labeling, cells were rinsed with ice-cold medium. Bound $^{32}$P was then quantitatively extracted with 1% SDS and 1% Triton X100 in PBS and counted in a Beckman LS5801 liquid scintillation counter.

LacZ$^+$ Virus (hrR3) Entry Assay:
Confluent Vero cell cultures in 96-well microtiter plates were switched to Hepes-buffered serum-free DMEM, cooled on ice to 4° C. for 30 min, and infected with hrR3 for 1 hour at 4° C. in 40 μl of medium. Unattached virus was removed by rinsing with ice-cold medium. Treatments with antiviral peptide SEQ ID NO:1, referred to as EB, or a control peptide which comprised the RRKK tetra-peptide (SEQ ID NO:16) attached to a scrambled version of the membrane transiting peptide R-R-K-K-L-A-A-L-P-L-V-L-A-A-P-L-A-V-L-A (SEQ ID NO:17) (referred to as EBX), or mock-treatments with peptide-free medium were carried out in serum-free DMEM as indicated. Virus entry was initiated by transferring cultures to 37° C. To inactivate any remaining extracellular virus, cultures were rinsed with PBS and exposed to low pH citrate buffer (40 mM citric acid, 10 mM KCl, 135 mM NaCl, pH 3.0, according to Highlander et al., *J. Virol.* 61:3356 (1987), for 1 min at 23° C. The citrate was rinsed off with PBS and cultures were maintained in serum-supplemented DMEM until they were fixed with 0.5% gluteraldehyde in 5×PBS for 30 min at 23° C., stained for β-galactosidase activity for 1 hour or overnight at 23° C. with X-gal (Fisher Biotech; BP1615-1) in 1×PBS containing 2 μM $MgCl_2$, 1.3 mM $K_4Fe(CN)_6$, and 1.3 mM $K_3Fe(CN)_6$, and scored for the presence of blue $lacZ^+$ cells.

Virucidal Assay:

HrR3 ($1.2\times10^6$ pfu/ml) was incubated with various concentrations of EB or EBX for 1 hour at 37° C. in 70 μl serum-free DMEM (pH 7.4). The treated virus was diluted 200-fold with serum-supplemented DMEM and assayed for infectivity approximately 1 hour later in microtiter wells seeded with Vero cells ($3.5\times10^4$ cells/well) 1 d earlier. Forty or 100 microliter volumes of diluted virus were adsorbed for 1 or 2 h at 37° C. and $lacZ^+$ cells were scored 8 hours later. In some experiments, aliquots of diluted virus were first dialyzed (Spectra/Por; MWCO 12-14,000) overnight at 4° C. against a 60-fold excess volume of Hepes-buffered serum-supplemented DMEM or forced by syringe through 0.22 μm membranes (Millex-GV; Millipore) before the remaining infectious virus was assayed.

Trypan-Blue Exclusion Assay:

Uninfected Vero cells in serum-free or serum-supplemented DMEM where treated for 1 hour at 37° C. with antiviral peptide SEQ ID NO:1 or control peptide EBX (SEQ ID NO:17), rinsed with PBS, stained for 5 min at 23° C. with 0.4% trypan-blue in PBS, rinsed again with PBS and air dried.

Electron Microscopy:

Purified HSV-1 KOS virions ($2.5\times10^7$ pfu/ml) according to Visalli et al., *Virus Res.* 29:167 (1993) were treated with 25 μM antiviral peptide SEQ ID NO:1 or the control peptide EBX (SEQ ID NO:17) in 40 μl serum-free DMEM buffered with 25 mM Hepes (pH 7.4) for 5 to 60 min at 4 or 23° C. Aliquots (10 μl) were adsorbed to pioloform poly-L-lysine-coated grids for 5 min at 23° C. Grids were rinsed with PBS, stained with 2% phosphotungstic acid (PTA) in water adjusted to pH ~6, and air dried. Alternatively, virus was pre-adsorbed to grids and treated with peptides thereafter. A total of $4\times10^9$ pfu/ml of purified HSV-1 KOS in 5 μl PBS was applied to the coated grids for 5 min at 23° C., and the grids were rinsed once with serum-free DMEM buffered with 25 mM Hepes (pH 7.4) and treated with 15 μl of 5 mM EB or EBX in the same medium for 30 min at 37° C. The pH of highly concentrated solutions of antiviral peptide SEQ ID NO:1 and EBX was re-adjusted to 7.4 with NaOH prior to use. To prevent evaporation of the peptide-containing solutions, each grid was held in a Hiraoka flexible staining plate and covered with miniature bell jar made from an 0.5 ml polypropylene micro-centrifuge tubes, small enough for the 15 μl to fill half of the bell jar facing the coated surface of the grid. The entire assembly was then incubated in a moist chamber for 30 min at 37° C. After treatment, grids were rinsed twice with DMEM and once with PBS before they were stained with PTA and dried. Grids were examined in a JEOL JEM-1200EX electron microscope at magnifications of 15,000 and 40,000×.

Peptide Synthesis:

Synthesis and analysis of peptides was done at the Biotechnology Center of the University of Wisconsin-Madison. Synthesis was carried out at a 25 pmole scale using an automated synthesizer (Applied Biosystems Model 432A "Synergy") following the principles initially described by Merrifield, *J. Am. Chem. Soc.* 85:7129 (1963) with modifications by Meienhofer et al., *Int. J. Peptide Protein Res.* 13:35 (1979) and Fields et al., *Peptide Res.* 4:95 (1991). The cleaved peptides were precipitated with cold t-butylmethylether, dissolved in water, and examined by analytical HPLC (purity) and electrospray ionization mass spectroscopy (molecular mass, see Table 1). Peptide concentrations in solution were determined from absorbance readings at 215 and 225 nm as taught by Segel, Biochemical Calculations, $2^{nd}$ ed. John Wiley & Sons, Inc., New York, N.Y. (1976).

Example 2

Antiviral Activity of Antiviral Peptides

Figures 1C, 1D:
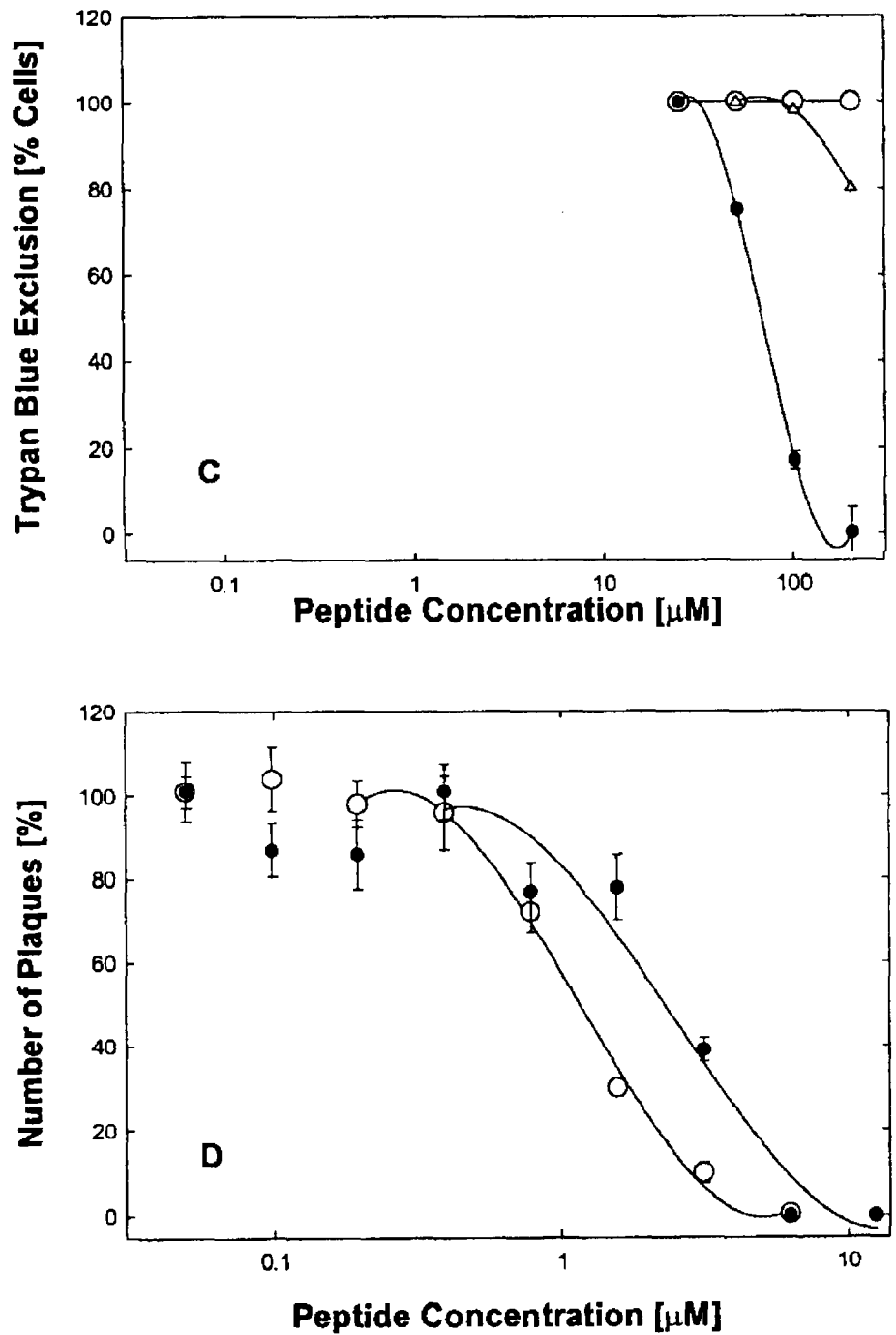
FIG. 1C shows the cytotoxic effects of SEQ ID NO:1 and SEQ ID NO:17.
Figure 1E:
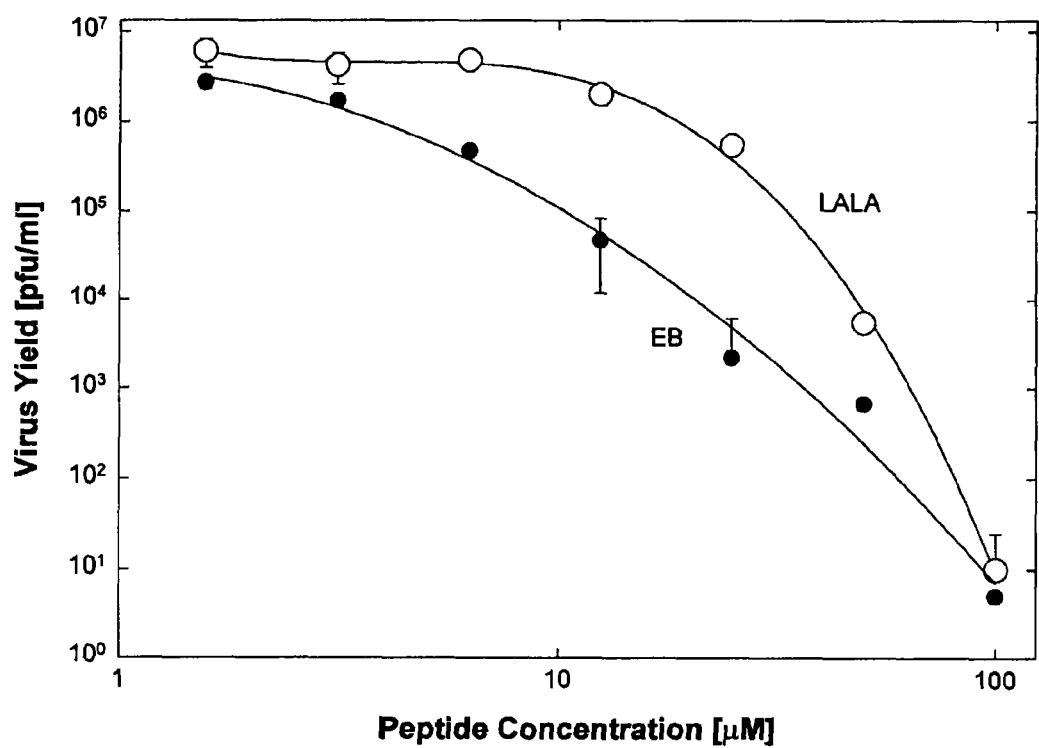

The antiviral peptide EB (SEQ ID NO:1), was an effective antiviral agent when present during infection of Vero cell cultures with HSV-1 KOS, blocking plaque formation as shown in FIG. 1A (●), FIG. 1B (●) and FIG. 1D (○); and reducing virus yields by up to eight orders of magnitude depending on concentration (see FIG. 1E). Compared to a control peptide FIG. 1A (○) and FIG. 1B (○) EBX, the antiviral peptide EB was a far more effective antiviral, blocking infections at 10 or 100-fold lower concentrations depending on the presence (FIG. 1A) or absence (FIG. 1B) of serum.

The cytotoxic effects of antiviral peptide EB, as measured by trypan-blue exclusion in the absence of serum, were seen only at concentrations 100-fold higher (FIG. 1C, (●); $IC_{50}$=68 μM) than antiviral concentrations (FIG. 1B, (●); $IC_{50}$=0.7 μM). In the presence of serum, cytotoxic effects were seen first at 200 μM EB (FIG. 1C, (Δ)). No cytotoxic effects were associated with the control peptide EBX (SEQ ID NO:17) (FIG. 1C, (○)).

The charged amino-terminal R-R-K-K tetramer was found to be useful for enhancing the solubility of the otherwise hydrophobic antiviral peptide EB, but does not have any important antiviral activity by itself. In the presence of serum, no antiviral activity was associated with the free R-R-K-K tetramer (SEQ ID NO:16) at concentrations as high as 200 μM (FIG. 1A, (▲)).

In separate experiments, it was discovered that free R-R-K-K tetramer (SEQ ID NO:16) inhibited hrR3 infection of Vero cells under serum-free conditions at an $IC_{50}$ value of 1.3 mM (data not shown). We also found that high (up to 100-fold molar excess), but non-antiviral concentrations of the free R-R-K-K peptide (SEQ ID NO:16) did not compete with antiviral peptide EB activity and could not relieve inhibition of hrR3 infections due to the antiviral peptide EB (data not shown).

To inquire whether derivatives of a membrane transiting protein sequence exhibited antiviral activity, we tested a modified antiviral peptide (SEQ ID NO:3) referred to as EBPP, in which the central proline residue was moved to the carboxy-terminal end. This EBPP-peptide (Table 1) was twice as active as the original EB peptide in both, plaque (FIG. 1D) and yield reduction assays (data not shown).

Figure 2:
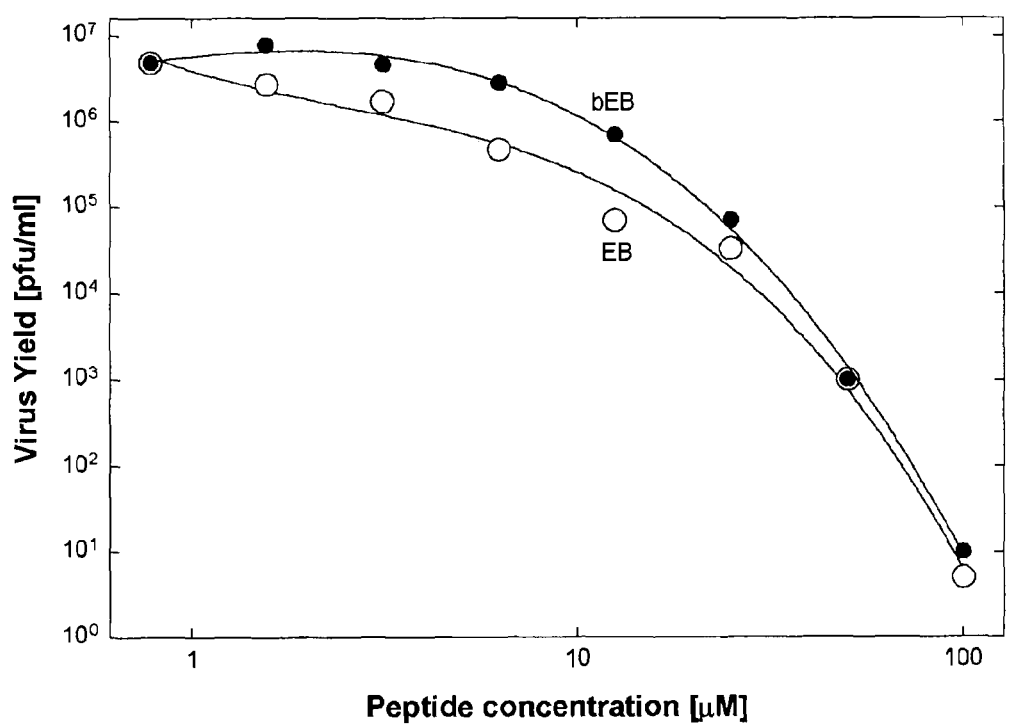
FIG. 2 is a graphical representation showing viral inhibition by a biotinylated antiviral peptide (SEQ ID NO:2) of the present invention.

The EB peptide was modified to carry biotin (SEQ ID NO:2), and tested for activity as described above. As shown in FIG. 2, the biotinylated EB was essentially as effective as EB. Thus biotinylation of the peptide had a negligible effect on activity.

The antiviral activity of a number of other antiviral peptides and controls according to the present invention were determined as described above. The results are shown below in Table 3. As shown in FIG. 1E, antiviral peptide SEQ ID NO:4, referred to as "LALA", demonstrates similar antiviral activity as EB.

TABLE 3

Antiviral Activity of Antiviral Peptides

| Peptide | Entry Blocking Activity[1] | Virucidal Activity[1] 37° C. | Virucidal Activity[1] 4° C. | Anti-Free Virus Activity[1] | Cyto-toxicity[1] |
|---|---|---|---|---|---|
| EB (SEQ ID NO: 1) | 15-26 | 44 | 89 | | |
| bEB (SEQ ID NO: 2) | 15 | 35 | 110 | 21 | 100 |
| EBX (SEQ ID NO: 17) | None | None | None | | |
| bKLA (SEQ ID NO: 5) | 11 | 15 | 45 | 4.5 | 15 |
| bKLAd$_{11,12}$ (SEQ ID NO: 6) | 23 | 61 | 300 | | |
| bHOM-9 (SEQ ID NO: 7) | 9-12 | 115 | None | 6 | 50 |
| bHOMd (SEQ ID NO: 8] | 7 | 115 | None | | |
| bHOMFF (SEQ ID NO: 9) | 40 | None | None | 34 | >>100 |
| bTAT-9 (SEQ ID NO: 10) | 26 | None | None | 8 | ~200 |
| bTAT-9x (SEQ ID NO: 12) | 67 | None | None | | |

[1]IC$_{50}$ values for all peptides

Example 3

Comparison of Antiviral Activity of Antiviral Peptide vs. Acyclovir

Figure 3:
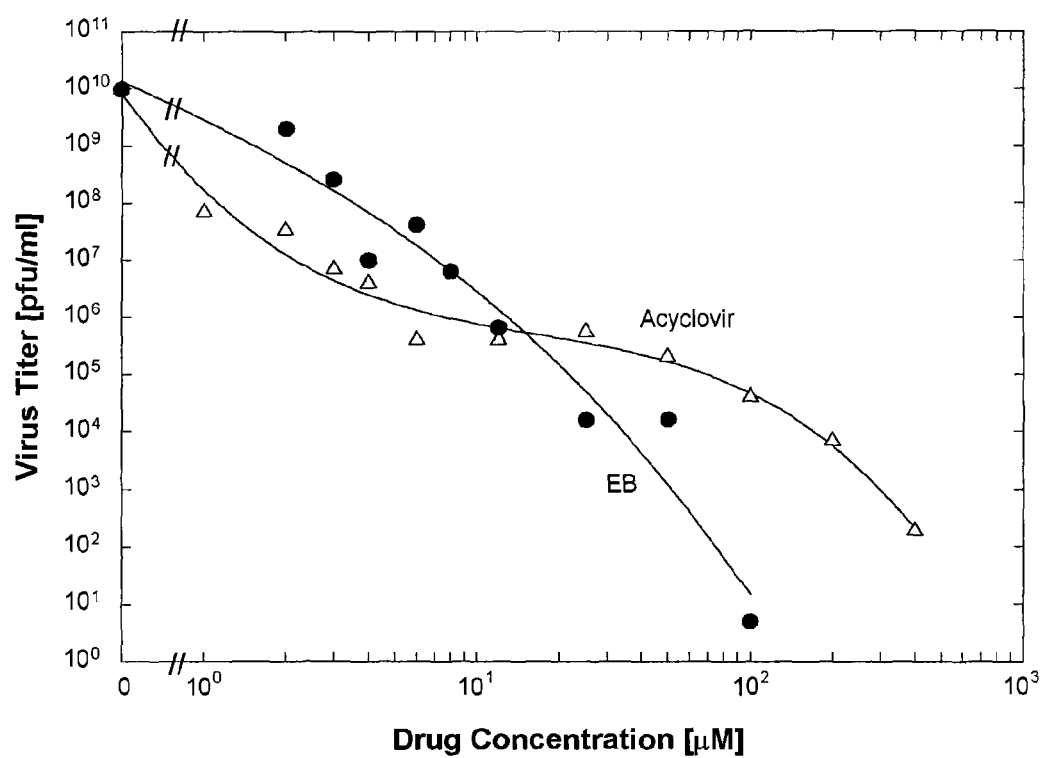
FIG. 3 is a graphical representation showing the dose-dependent inhibition of HSV-1 formation by an antiviral peptide of the present invention (SEQ ID NO:1) as compared to acylovir.

Vero cell cultures as prepared in Example 1 were infected with HSV-1 and assayed for virus production as described in Example 1. The antiviral activity of an antiviral peptide according to the present invention EB (SEQ ID NO:1) was compared to the antiviral activity of the current HSV antiviral nucleoside standard, acyclovir. The two peptides were added to the Vero cells one hour prior to infection with HSV. As FIG. 3 illustrates, although acyclovir shows the highest antiviral activity at low dosages, at high concentrations, i.e., those exceeding 10 µM of the active ingredient, EB showed the greatest antiviral activity.

Example 4

Early Effects and Effects on Cell-Cell Spreading

Figures 4A, 4B:
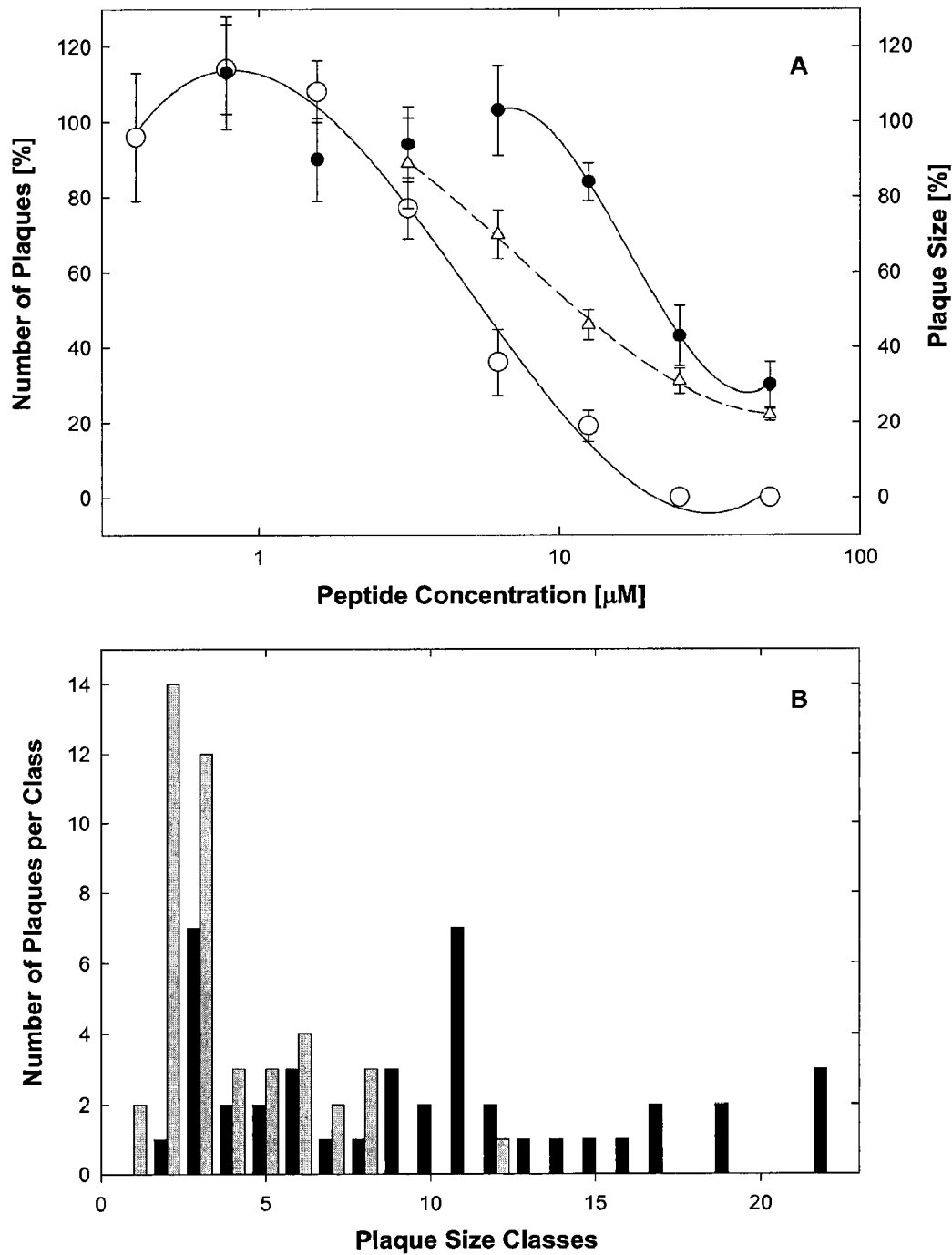
FIGS. 4A and 4B are graphs illustrating that an antiviral peptide of the present invention (SEQ ID NO:1) inhibits an early stage of virus infection and virus spreading.

It was determined that antiviral peptides according to the present invention act early in the viral life cycle. As shown in FIG. 4A, EB was substantially more effective, when present during infection and 1 hour pre- and post-infection, than when present continuously starting 1 hour post-infection (IC$_{50}$=5.5 µM, (○) vs. IC$_{50}$=24, (●)), respectively). Furthermore, when present before and during adsorption, EB had no effect on plaque size. When the EB peptide was present continuously after infection, plaque expansion was inhibited in a dose-dependent manner (FIG. 4A, (Δ); IC$_{50}$=12 µM). To ensure that individual plaques were measured reliably, cell cultures were infected at very low multiplicity (moi<0.01) and plaque sizes were measured microscopically very early (1 day post-infection). As shown in FIG. 4B, in untreated control wells, plaque size was broadly distributed (black bars; mean: 66,000±6200 µm$^2$), whereas addition of increasing concentrations of EB 1 hour post-infection progressively shifted the distribution towards smaller size classes (e.g., 25 µM EB significantly reduced the mean plaque size by 70% to 6900±2600 µm$^2$; t=6.88; shaded bars). In contrast, the presence of EB up to 1 hour post-infection had no effect on plaque size, even though the number of plaques were severely reduced compared to post-infection treatment. Thus, the combined mean plaque size after transient treatments with 6 and 12 µM EB (68,000±11,000 µm$^2$), was indistinguishable from the controls. EB appeared to act at an early stage of viral infection and reduced plaque size when added after infection.

Example 5

Aggregation of Virus by Antiviral Peptide

Antiviral peptides of the present invention were shown to aggregate virus by electron microscopy. Purified virus particles at high concentrations, as required for efficient visualization, were incubated with 25 µM EB, adsorbed to coated grids and stained with PTA. The results showed nearly all of the particles were seen in relatively few large aggregates. In contrast, untreated virus, or virus particles treated with 25 µM EBX were nearly all found individually and uniformly scattered over the grid surface. The individual PTA-stained virus particles within aggregates were virtually indistinguishable from control particles, indicating that EB did not induce gross structural abnormalities in the virus particles. The EB-induced aggregates were formed rapidly (<5 min) at room temperature as well as at 4° C.

Example 6

Antiviral Activity of Antiviral Peptide with Respect to Virus Input

Figure 5:
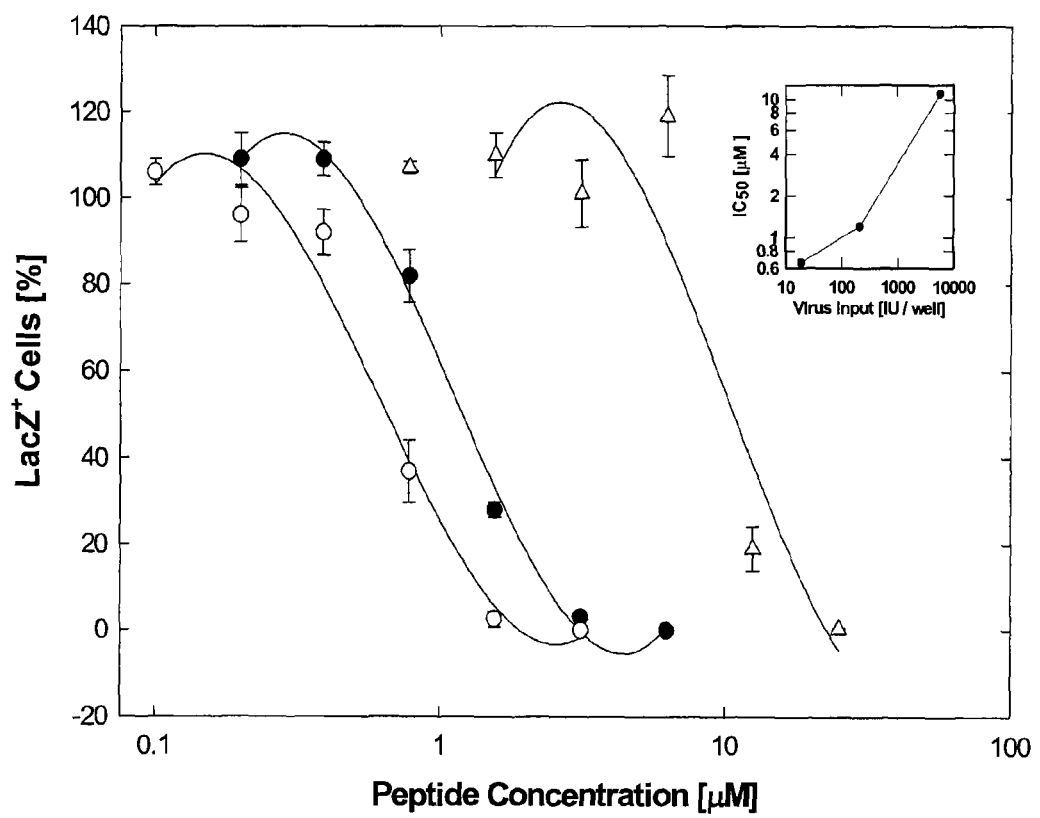
FIG. 5 is a graph illustrating the antiviral activity of an antiviral peptide of the present invention (SEQ ID NO:1) is dependent on virus input.

Cultures were infected with hrR3 at inputs of 19, 210, and 5700 pfu/well in the presence of various concentrations of EB and scored 8 hours later for lacZ$^+$ cells, the IC$_{50}$ values obtained were 0.66, 1.2, and 11 µM, respectively, as shown in FIG. 5.

Significantly, above the intermediate input of 210 pfu/well, there was a greater increase in the IC$_{50}$ with increasing virus titer than below that input, as shown in the inset in FIG. 5. The inverse relationship between IC$_{50}$ and virus titer would be expected if EB merely acted as an aggregation agent, which should operate more efficiently, i.e., with lower IC$_{50}$, at the higher virus input. Thus, viral aggregation does not make any major contribution to the antiviral activity of EB in these experiments. Furthermore, the fact that the antiviral activity of EB strongly depended on virus concentrations, suggests that that the antiviral peptides of the present invention interact with viral components.

Example 7

Inhibition of Viral Entry

Additional studies with pre-adsorbed hrR3 virus demonstrated that the antiviral effect or effects of an antiviral peptide of the present invention are related neither to virus adsorption nor to virus aggregation, but rather to inhibition of virus entry. In these studies, the hrR3 virus was pre-adsorbed to cells for 1 hour at 4° C. before ice cold 25 µM EB or EBX were added in serum-free DMEM. After an additional 1 hour at 4° C., cultures were shifted to 37° C. to initiate virus entry. At 15 min intervals following the temperature shift, any virus remaining outside the cells was inactivated by washing the cultures with low pH citrate buffer. Cultures were then rinsed and returned to peptide-free serum-supplemented DMEM until they were fixed and stained for β-galactosidase 8 hours after the temperature shift.

Figures 6A, 6B:
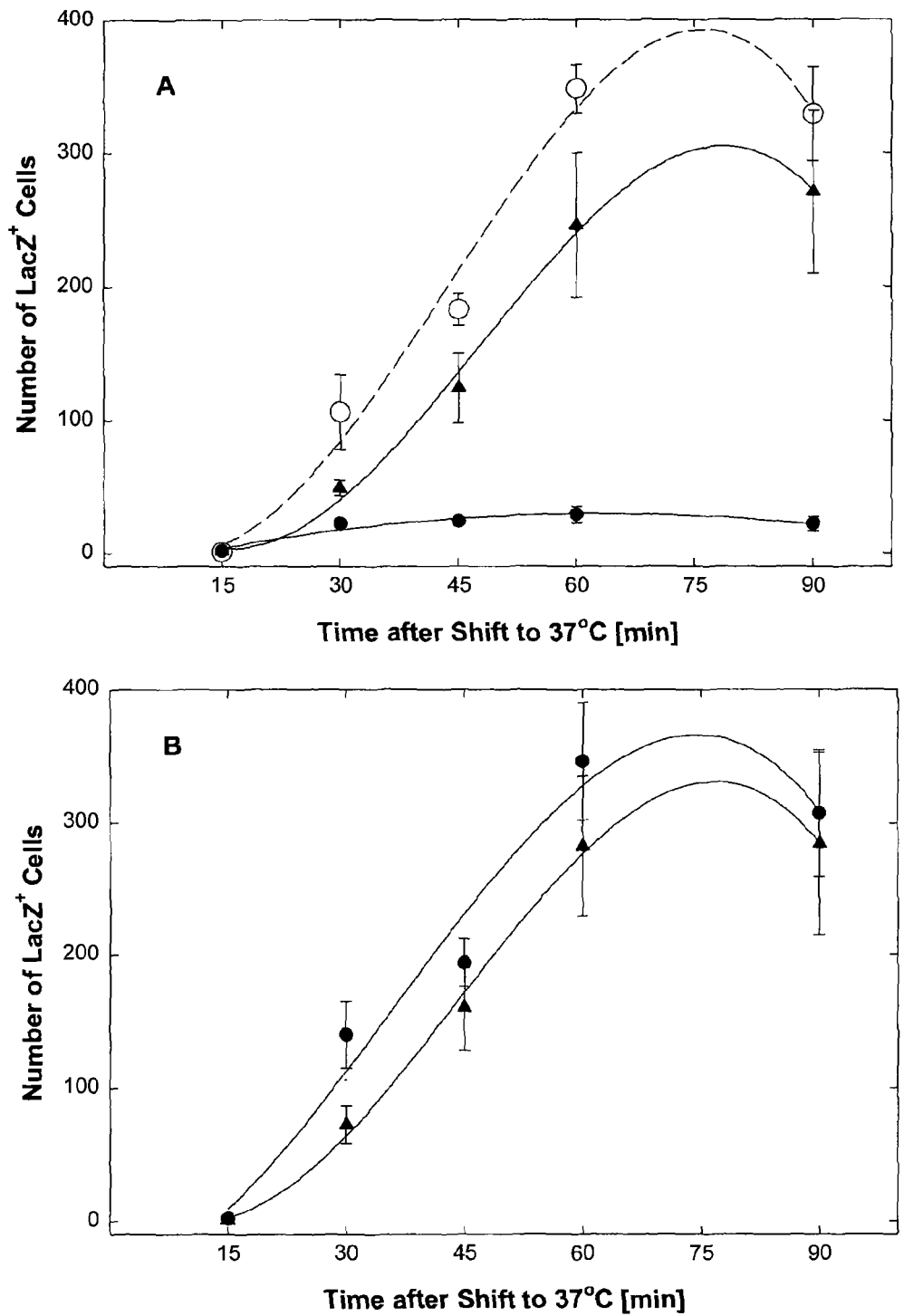
FIGS. 6A and 6B are graphs illustrating the blocking of viral entry into cells by an antiviral peptide of the present invention (SEQ ID NO:1).

As shown in FIG. 6A, virus entry in mock-treated control cultures (○) was initiated 15-30 min after transfer to 37° C. and completed by about 60 min at a level of about 340 lacZ$^+$ cells per 6.5 mm$^2$ (or 1450 lacZ$^+$ cells/well). In cultures treated with the EB peptide, the number of lacZ$^+$ cells was reduced by >90% (●). The EBX peptide did not significantly reduce the number of lacZ$^+$ cells (▲). Essentially the same results were obtained when EB and EBX were added prior to virus adsorption (data not shown). When peptide was added immediately after each citrate treatment, EB no longer had any effect on the development of lacZ$^+$ cells (FIG. 6B, (●); cf. FIG. 6A, (○)). EBX also did not significantly inhibit the development of lacZ$^+$ cells when added immediately after the citrate treatments (FIG. 6B, (▲)). Thus, EB had no effect on the expression of the lacZ gene from the early ICP6 promoter, but selectively blocked viral entry.

Figures 7A, 7B:
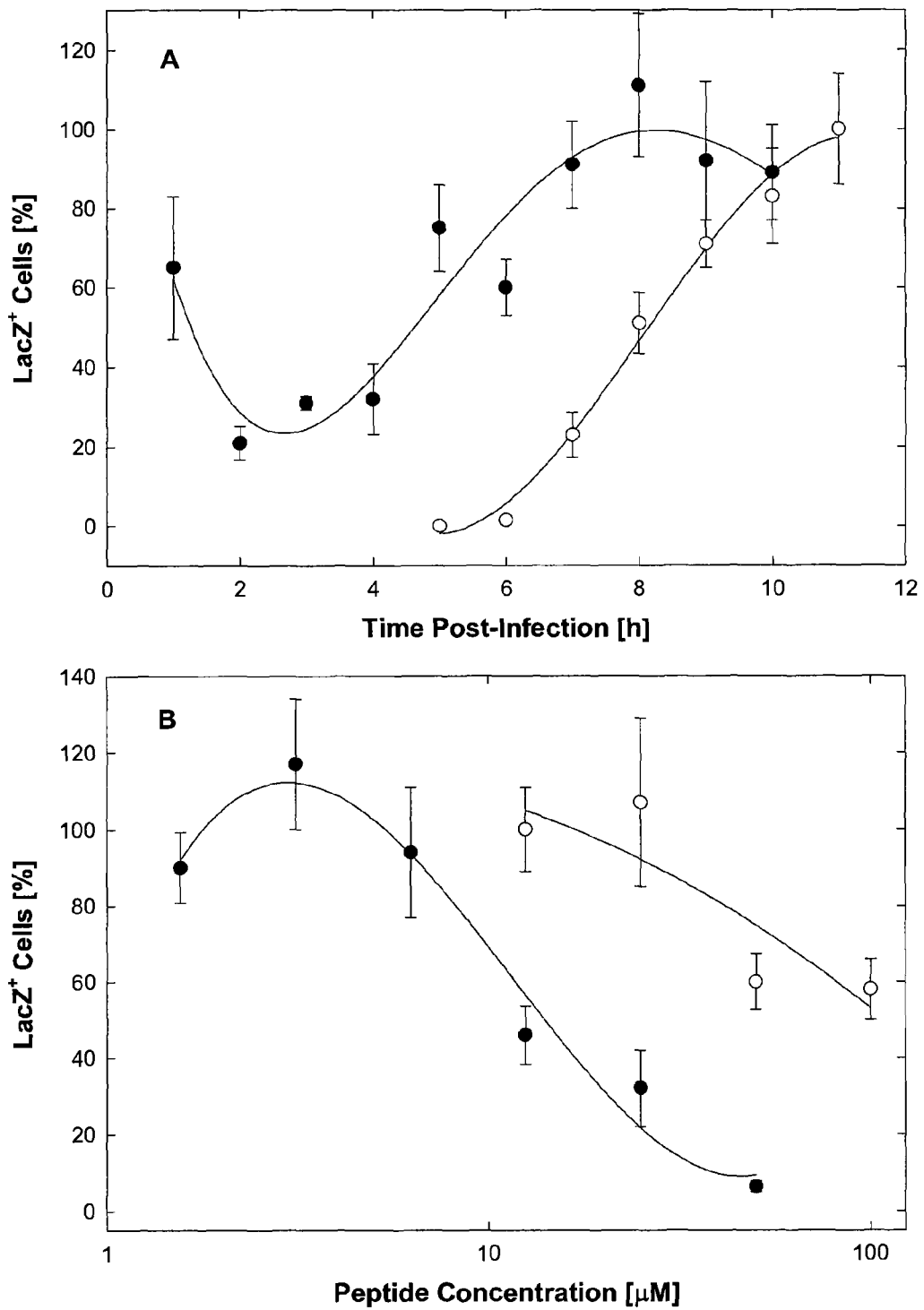
FIGS. 7A and 7B are graphs illustrating the entry phase and dose response of an antiviral peptide of the present invention (SEQ ID NO:1).

This conclusion is strengthened by the finding that the EB-sensitive phase of infection with pre-adsorbed virus clearly precedes expression of lacZ genes in hrR3 infected cells (FIG. 7A). Again, hrR3 was pre-adsorbed to cells for 1 hour at 4° C., unattached virus was rinsed off, and cells were kept for an additional hour at 4° C. Cultures were then transferred to 23° C. for 30 mm before they were switched to 37° C. The more gradual change to 37° C. allowed cell layers to remain intact through subsequent frequent medium changes. Immediately following viral adsorption, cells were treated with 50 µM EB for 1 hour periods at consecutive 1 hour intervals. Between 1 and 4 hours post-infection, virus entry was inhibited by 70-80%. Thereafter, infection was no longer significantly inhibited (FIG. 7A, (●)). Parallel cultures were immediately fixed after mock-treatments and stained with X-gal. In these cultures, blue (lacZ$^+$) cells first appeared 7 hours post-infection and their number increased nearly linearly for the next 3 hours (FIG. 7A, (○)). By 7 hours post-infection, EB ceased to be inhibitory. Thus, EB only blocked virus entry during an early brief sensitive period and had no effect on the expression of the lacZ gene and the development of β-galactosidase activity once the virus had entered the cell. As shown in FIG. 7B, EB inhibited entry of pre-adsorbed virus in a dose-dependent manner with an IC$_{50}$=15 µM (●), whereas EBX was less effective (IC$_{50}$~100 µM; (○)).

Example 8

Virucidal Effects of Antiviral Peptide

Figures 8A, 8B:
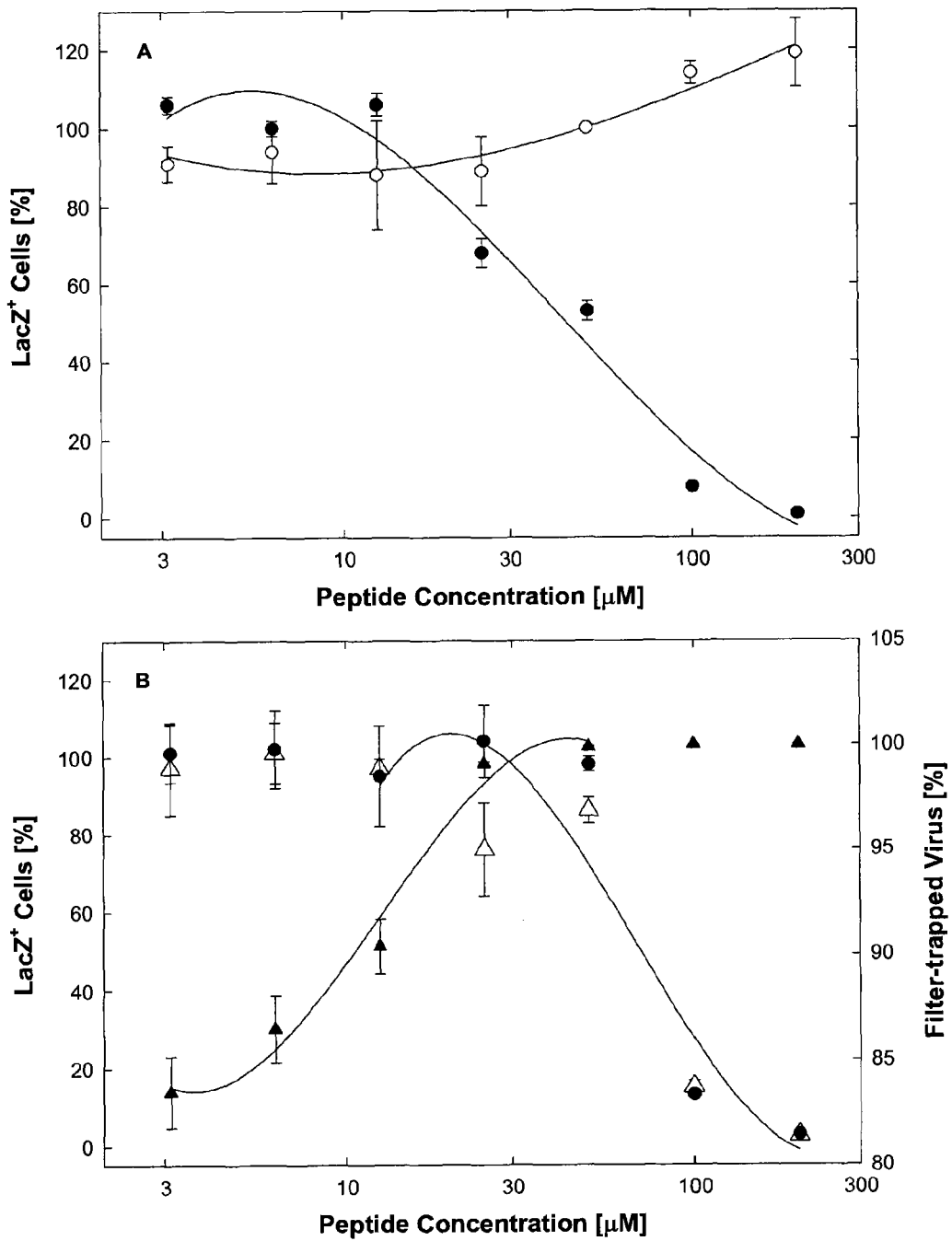
FIGS. 8A and 8B are graphs illustrating the virucidal activity of an antiviral peptide of the present invention (SEQ ID NO:1).

It was found that the binding of antiviral peptides of the present invention to virus particles leads to irreversible virus inactivation. Virucidal assays were performed with hrR3. In the first experiment (FIG. 8A), EB inhibited the infectivity of virions in a concentration-dependent manner with an IC$_{50}$=44 µM (●), whereas EBX had no inhibitory effect (○). In the second experiment, in which slightly higher concentrations of EB were required to achieve inhibition (FIG. 8B, (●); IC$_{50}$=69 µM), we also found that the treated virions were irreversibly inactivated. That is, aliquots of EB-treated and then diluted virions could not be re-activated during overnight dialysis against serum-containing medium that could have trapped any reversibly-bound EB (cf. FIG. 1, (●); A vs. B). Instead, virions recovered after dialysis (31% at any EB concentration) remained inactivated exactly like the non-dialyzed controls (FIG. 8B, (Δ) vs. (●)).

To assess possible contributions of viral aggregation to viral inactivation, additional aliquots of EB-treated and subsequently diluted virions were filtered through 0.22 µm membranes before they were assayed for remaining infectivity. In the absence of, or at low concentrations of EB (≤3 µM), 80-85% of the virions were trapped on the membranes. The remaining virions, however, were retained only once exposed to higher EB concentrations, which enhanced membrane adhesion and/or caused viral aggregation (FIG. 8B, (▲)). Such changes in the adhesive properties of virions were induced well below EB concentrations required for virus inactivation (FIG. 8B, (▲) vs. (●), (Δ)).

The effects of the most severe EB treatments were examined by electron microscopy of PTA-stained virions that had been pre-adsorbed to grids (to avoid aggregation) and exposed to 5 mM of peptide. The EB-treated virions looked essentially the same as mock-treated virions, except that contours of the viral envelops in the EB-treated particles were less pleomorphic, suggesting EB stabilized virions. At 5 mM, EBX had the same effect as EB.

Example 9

In Vivo Activity of Antiviral Peptide

The antiviral peptides according to the present invention demonstrate in vivo activity when topically applied. HSV-1 strain KOS was incubated for 1 hour with either the EB peptide or the EBX peptide at a concentration of 25 µM at room temperature in PBS. Groups of ten mice each were then infected via corneal scarification with 5.0×10⁵ plaque forming units as we have described previously (Brandt et. al., J. Virol. Meth. 36, 209 (1992).

Briefly, the mice were anesthetized with halothane, the cornea was scratched 3 times horizontally and 3 times vertically, and a 5 µl drop containing virus was placed on the cornea. The mice were then returned to their cages and allowed to recover. A control group infected with KOS but not exposed to peptide was also included. The mice were not treated with peptide after infection.

Figures 9A, 9B:
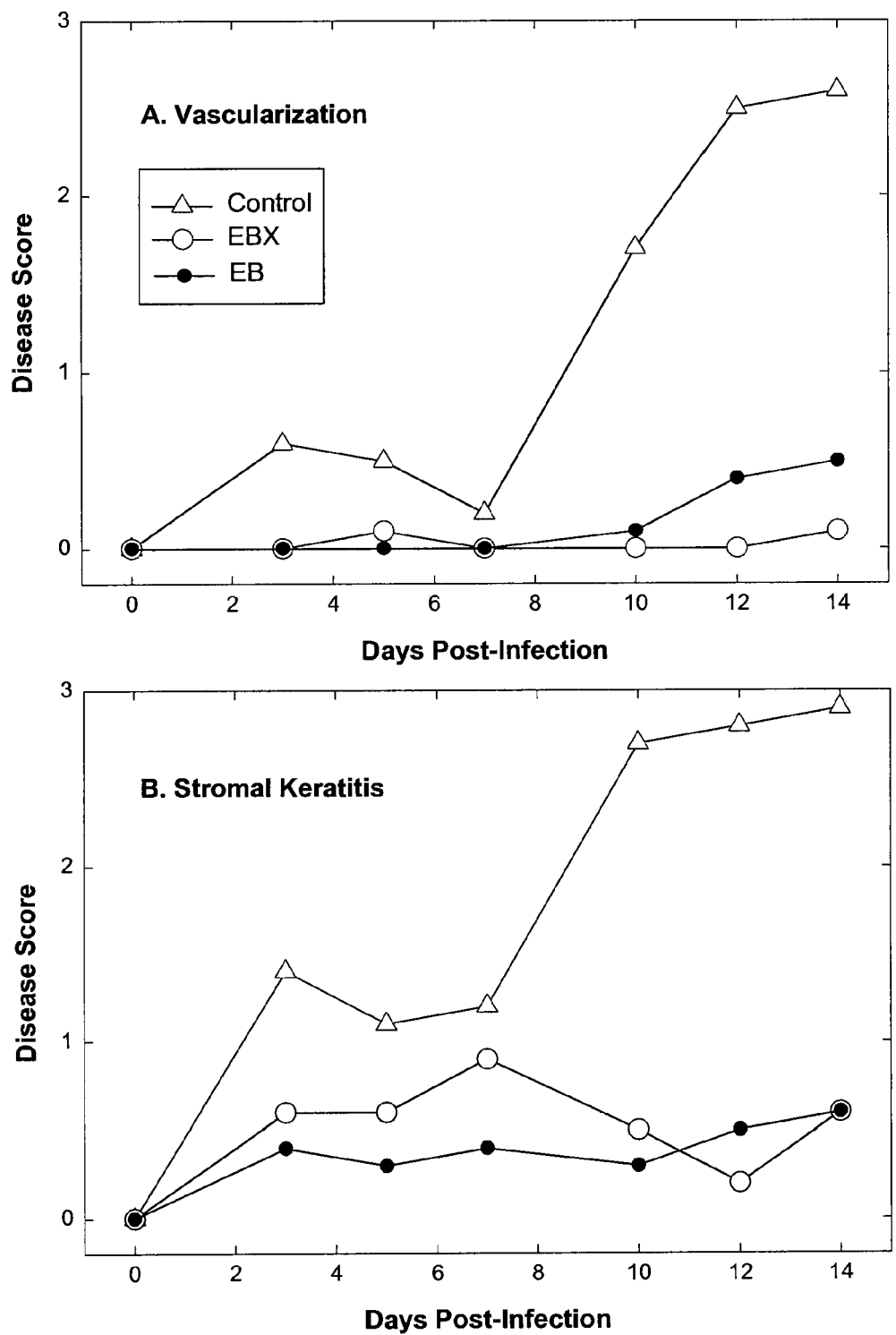
FIGS. 9A and 9B are graphs illustrating the in vivo activity of an antiviral peptide of the present invention (SEQ ID NO:1).

At various times post-infection, the severity of ocular disease was measured as we described previously (same ref.) Briefly, vascularization was scored: 0, no vascularization; 1+<25% of the cornea involved; 2+25-50% involvement; and 3+>50% involvement (see FIG. 9A). Keratitis was scored: 0 no corneal clouding; 1+cloudiness, some iris detail visible; 2+cloudy, iris detail obscured; 3±cornea totally opaque; 4+cornea perforated and cloudy (see FIG. 9B). Data are reported as the mean disease score on each day for each of the three groups. The results are illustrated in FIG. 9.

The following references are additionally incorporated by reference:

1. Aldrian-Herrada, G., M. G. Desarménien, H. Orcel, L. Boissin-Agasse, J. Méry, J. Brugidou, and A. Rabié. 1998. A peptide nucleic acid (PNA) is more rapidly internalized in cultured neurons when coupled to a retro-inverso delivery peptide. The antisense activity depresses the target mRNA and protein in magnocellular oxytocin neurons. *Nucleic Acids Res*. 26:4910-4916.
2. Banfield, B. W., Y. Leduc, L. Esford, R. J. Visalli, C. R. Brandt, and F. Tufaro. 1995. Evidence for an interaction of herpes simplex virus with chondroitin sulfate proteoglycans during infection. *Virology* 208:531-539.
3. Berkowitz, B. A., C. L. Bevins, and M. A. Zasloff. Magainins: A new family of membrane-active host defense peptides. *Biochem. Pharmacol*. 39:625-629, 1990.
4. Cai, W., B. Gu, and S. Person. 1988. Role of glycoprotein B of herpes simplex virus type I in viral entry and fusion. *J. Virol*. 62:2596-2604.
5. Campadelli-Fiume, G., D. Stirpe, A. Boscano, E. Avitabile, L. Foa-Tomasi, D. Barker, and B. Roizman. 1990. Glycoprotein C-dependent attachment of herpes simplex virus to susceptible cells leading to productive infection. *Virology* 178:213-222.
6. Chou, P. Y. and G. D. Fasman. 1978. Prediction of the secondary structure of proteins from their amino acid sequence. *Adv. Enzymol Related Areas Mol. Biol*. 47: 45-147.
7. Cockrell, A. S., and M. I. Muggeridge. 1998. Herpes simplex virus type 2 UL45 is a type H membrane protein. *J. Virol*. 72:4430-4433.
8. Coen, D. M., D. P. Aschman, P. T. Gelep, M. J. Retondo, S. K. Weller, and P. A. Schaffer. 1984. Fine mapping and molecular cloning of mutations in the herpes simplex virus DNA polymerase locus. *J. Virol*. 49:236-247.
9. Derossi, D., A. H. Joliot, G. Chassaing, and A. Prochiantz. 1994. The third helix of the antennapedia homeodomain translocates through biological membranes. *J. Biol. Chem*. 269:1044-1050.
10. Desai, P. J., P. A. Schaffer, and A. C. Minson. 1988. Excretion of non-infectious virus particles lacking gH by a temperature-sensitive mutant of herpes simplex virus type I: Evidence that gH is essential for virion infectivity. *J. Gen. Virol*. 69:1147-1156.
11. Fawell, S., J. Seery, Y. Daikh, C. Moore, L. L. Chen, B. Pepinsky, and J. Barsoum. 1994. Tat-mediated delivery of heterologous proteins into cells. *Proc. Natl. Acad. Sci. USA* 91:664-668.
12. Fields, C. G., D. H. Lloyd, R. L. Macdonald, K. M. Otteson, and R. L. Noble. 1991. HBTU activation for automated Fmoc solid-phase peptide synthesis. *Peptide Res*. 4:95-101.
13. Fuller, A. D., and P. G. Spear. 1987. Anti-glycoprotein D antibodies that permit adsorption but block infection by herpes simplex virus 1 prevent virion-cell fusion at the cell surface. *Proc. Natl. Acad. Sci. USA* 84:5454-5458.
14. Fuller, A. O., and W.-C. Lee. 1992. Herpes simplex virus type I entry through a cascade of virus-cell interactions requires different roles of gD and gH in penetration. *J. Virol*. 66:5002-5012.
15. Geraghty, R. J., C. Krummenacher, G. Cohen, R. J. Eisenberg, and P. G. Spear. 1998. Entry of alphaherpesviruses mediated by poliovirus receptor related protein 1 and poliovirus receptor. *Science* 280:1618-1620.
16. Gibbs, J. S., H. C. Chiou, J. D. Hall, D. W. Mount, M. J. Retondo, S. K. Weller, and D. M. Coen. 1985. Sequence and mapping analysis of the herpes simplex virus DNA polymerase gene predicts a c-terminal substrate binding domain. *Proc. Natl. Acad. Sci. USA* 82:7969-7973.
17. Grau, D. R., R. J. Visalli, and C. R. Brandt. 1989. Herpes simplex virus stromal keratitis is not titer-dependent and does not correlate with neurovirulence. *Invest. Ophthalmol. Vis. Sci*. 30:2474-2480.
18. Haanes, E. J., C. M. Nelson, C. L. Soule, and J. L. Goodman. 1994. The UL45 gene product is requires for herpes simplex virus type 1 glycoprotein B-induced fusion. *J. Virol*. 68:5825-5834.
19. Hall, J. D., and S. Woodward. 1989. Aphidicolin resistance in herpes simplex virus type 1 appears to alter substrate specificity in the DNA polymerase. *J. Virol*. 63:2874-2876.
20. Handler, C. G., G. Cohen, and R. J. Eisenberg. 1996. Cross-linking of glycoprotein oligomers during herpes simplex virus type 1 entry. *J. Virol*. 70:6076-6082.
21. Herold, B. C., D. WuDunn, N. Soltus, and P. G. Spear. 1991. Glycoprotein C of herpes simplex virus type 1 plays a principal role in the adsorption of virus to cells and in infectivity. *J. Virol*. 65:1090-1098.
22. Herold, B. C., R. J. Visalli, N. Susmarski, C. R. Brandt, and P. G. Spear. 1994. Glycoprotein C-independent binding of herpes simplex virus to cells requires cell surface heparan sulphate and glycoprotein B. *J. Gen. Virol*. 75:1211-1222.
23. Herold, B. C., S. I. Gerber, B. J. Belval, A. M. Siston, and N. Shulman. 1996. Differences in the susceptibility of Herpes simplex virus types 1 and 2 to modified heparan compounds suggest serotype differences in viral entry. *J. Virol*. 70:3461-3469.
24. Highlander S, Sutherland S L, Gage P J, D. C. Johnson, M. Levine, and J. C. Glorioso. 1987. Neutralizing monoclonal antibodies specific for herpes simplex virus glycoprotein D inhibit virus penetration. *J. Virol*. 61:3356-3364.
25. Hutchinson, L., L. K. Goldsmith, H. Browne, V. Wargent, N. Davis-Poynter, S. Primorac, K. Goldsmith, A. C. Minson, and D. C. Johnson. 1992. A novel herpes simplex virus type 1 glycoprotein forms a complex with glycoprotein H (gH) and affects normal folding and surface expression of gH. *J. Virol*. 66:2240-2250.
26. Johnson, D. C., and P. G. Spear. 1989. Herpes simplex virus glycoprotein D mediates interference with herpes simplex virus infection. *J. Virol*. 63:819-827.

27. Kilby, M. J., S. Hopkins, T. M. Venetta, B. DiMassimo, G. A. Cloud, J. Y. Lee, L. Alldredge, E. Hunter, D. Lambert, D. Bolognesi, T. Matthews, M. R. Johnson, M. A. Nowak, G. M. Shaw, and M. S. Saag. 1998. Potent suppression of HIV-1 replication in humans by T-20, a peptide inhibitor of gp41-mediated virus entry. *Nature Med.* 11:1302-1307.

28. Knopf, C. W. 1987. The herpes simplex virus type 1 DNA polymerase gene: Site of phosphonoacetic acid resistance mutation in strain Angelotti is highly conserved. *J. Gen. Virol.* 68:1429-1433.

29. Krummenacher, C., A. V. Nicola, J. C. Whitbeck, H. Lou, W. Hou, J. D. Lambris, R. J. Geraghty, P. G. Spear, G. H. Cohen, and R. J. Eisenberg. 1998. Herpes simplex virus glycoprotein D can bind to poliovirus receptor-related protein 1 or herpesvirus entry mediator, two structurally unrelated mediators of virus entry. *J. Virol.* 72:7064-7074.

30. Laquerre, S., R. Argnani, D. B. Anderson, S. Zucchini, R. Manservigi, and J. C. Glorioso. 1998. Heparan sulfate proteoglycan binding by herpes simplex virus type 1 glycoproteins B and C, which differ in their contributions to virus attachment, penetration, and cell to cell spread. *J. Virol.* 72:6119-6130.

31. Ligas, M. W., and D. C. Johnson. 1988. A herpes simplex virus mutant in which glycoprotein D sequences are replaced by β-galactosidase sequences binds to, but is unable to penetrate into cells. *J. Virol.* 62:1486-1494.

32. Lin, Y, -Z., S.-Y. Yao, R. A. Veach, T. R. Torgerson, and J. Hawiger. 1995. Inhibition of nuclear translocation of transcription factor NF-κβ by a synthetic peptide containing a cell membrane-permeable motif and nuclear localization sequence. *J. Biol. Chem.* 270:14255-14258.

33. Lycke, E., M. Johansson, B. Svennerholm, and U. Lindahl. 1991. Binding of herpes simplex virus to cellular heparan sulfate, an initial step in the adsorption process. *J. Gen. Virol.* 72:1131-1137.

34. Manservigi, R., P. G. Spear, and A. Buchan. 1977. Cell fusion induced by herpes simplex virus is promoted and suppressed by different viral glycoproteins. *Proc. Natl. Acad. Sci. USA* 74:3913-3917.

35. Matthews, J. T., B. J. Terry, and A. K. Field. 1993. The structure and function of the HSV DNA replication proteins: Defining novel antiviral targets. *Antiviral Res.* 20:89-114.

36. Meienhofer, J., M. Waki, E. P. Heimer, T. J. Lambros, R. C. Makofske, and C. D. Chang. 1979. Solid phase synthesis without repetitive acidolysis: Preparation of leucyl-alanyl-glycyl-valine using 9-fluorenylmethyloxycarbonylamino acids. *Int. J. Peptide Protein Res.* 13:35-42.

37. Merrifield, R. B. 1963. Solid phase peptide synthesis I. The synthesis of a tetrapeptide. *J. Am. Chem. Soc.* 85:7129-7133.

38. Minson, A. C., T. C. Hodgman, P. Digard, D. C. Hancock, S. E. Bell, and E. A. Buckmaster. 1986. An analysis of the biological properties of monoclonal antibodies against glycoprotein D of herpes simplex virus and identification of amino acid substitutions that confer resistance to neutralization. *J. Gen. Virol.* 67:1001-1013.

39. Montgomery, R. I., M. S. Warner, B. J. Lum, and P. G. Spear. 1996. Herpes simplex virus-1 entry into cells mediated by a novel member of the TNF/NGF receptor family. *Cell* 87:427-436.

40. Nicola, A. V., S. H. Willis, N. Naidoo, R. J. Eisenberg, and G. Cohen. 1996. Structure function analysis of soluble forms of herpes simplex virus glycoprotein D. *J. Virol.* 70:3815-3822.

41. Nicola, A. V., M. Ponce de Leon, R. Xu, W. Hou, J. C. Whitbeck, C. Krummenacher, R. I. Montgomery, P. G. Spear, R. J. Eisenberg, and G. H. Cohen. 1998. Monoclonal antibodies to distinct sites on herpes simplex virus (HSV) glycoprotein D block HSV binding to HVEM. *J. Virol.* 72:3595-3601.

42. Nisole, S., B. Krust, C. Callebaut, G. Guichard, S. Muller, J.-P. Briand, and A. G. Hovanessian. The anti-HIV pseudopeptide HB-19 forms a complex with the cell-surface-expressed nucleolin independent of heparan sulfate proteoglycans. *J. Biol. Chem.* 274:27875-27884.

43. Oehlke, J., E. Krause, B. Wiesner, M. Beyermann, and M. Bienert. 1996. Nonendocytic, amphipathicity dependent cellular uptake of helical model peptides. *Protein Peptide Lett.* 3:393-398.

44. Oehlke, J., E. Krause, B. Wiesner, M. Beyermann, and M. Bienert. 1997. Extensive cellular uptake into endothelial cells of an amphipathic β-sheet forming peptide. *FEBS Lett.* 415:196-199.

45. Pooga, M., M. Hällbrink, M. Zorko, and Ü Langel. 1998. Cell penetration by transportan. *FASEB J* 12:67-77.

46. Rimsky, L. T., D. C. Shugars, T. J. Matthews. 1998. Determinants of human immunodeficiency virus type 1 resistance to gp41-derived inhibitory peptides. *J. Virol.* 72:986-993.

47. Roop, C., L. Hutchinson, and D. C. Johnson. 1993. A mutant herpes simplex virus type 1 unable to express glycoprotein L cannot enter cells and its particles lack glycoprotein H. *J. Virol.* 67:2285-2297.

48. Sasadeusz, J. J., F. Tufaro, S. Safrin, K. Schubert, M. M. Hubinette, P. K. Cheung, and S. L. Sacks. 1997. Homopolymer mutational hot spots mediate herpes simplex virus resistance to acyclovir. *J. Virol.* 71:3872-3878.

49. Schwarze, S. R., A. Ho, A. Vocero-Akbani, and S. F. Dowdy. 1999. In vivo protein transduction: Delivery of a biologically active protein into the mouse. *Science* 285:1569-1572.

50. Sears, A. E., B. S. McGwire, and B. Roizman. 1991. Infection of polarized MDCK cells with herpes simplex virus 1: Two asymetrically distributed cell receptors interact with different viral proteins. *Proc. Natl. Acad. Sci. USA* 88:5087-5091.

51. Segel, I. H. 1976. Biochemical Calculations, $2^{nd}$ ed. John Wiley & Sons, Inc., New York, N.Y.

52. Shieh, M. T., D. WuDunn, R. L Montgomery, J. D. Esko, and P. G. Spear. 1992. Cell surface receptors for herpes simplex virus are heparan sulfate proteoglycans. *J. Cell Biol.* 116:1273-1281.

53. Shieh, M. T., and P. G. Spear. 1994. Herpes virus-induced cell fusion that is dependent on cell surface heparan sulfate or soluble heparan. *J. Virol.* 68:1224-1228.

54. Spear, P. G. 1993. Entry of alphaherpesviruses into cells. *Sem. Virol.* 4:167-180.

55. Srinivas, R. V., B. Birkedal, R. J. Owens, G. M. Anantharamaiah, J. P. Segrest, and R. W. Compans. 1990. Antiviral effects of apolipoprotein A-I and its synthetic amphipathic peptide analogs. *Virology* 176:48-57.

56. Srinivas, S. K., R. V. Srinivas, G. M. Anantharamaiah, J. P. Segrest, and R. W. Compans. 1992. Membrane interactions of synthetic peptides corresponding to amphipathic helical segments of the human immunodeficiency virus type-1 envelope glycoprotein. *J. Biol. Chem.* 267:7121-7127.

57. Tal-Singer, R., C. Peng, M. Ponce de Leon, W. R. Abrams, B. W. Banfield, F. Tufaro, G. H. Cohen, and R. J. Eisenberg. 1995. Interaction of herpes simplex virus glycoprotein C with mammalian cell surface molecules. *J. Virol.* 69:4471-4483.

58. Théodore, L., D. Derossi, G. Chassaing, B. Llirbat, M. Kubes, P. Jordan, H. Chneiweiss, P. Godement, and A.

Prochiantz. 1995. Intraneuronal delivery of protein kinase C pseudosubstrate leads to growth cone collapse. *J. Neurosci.* 15:7158-7167.

59. Turner, A., B. Bruun, T. Minson, and H. Browne. 1998. Glycoproteins gB, gD, and gHgL of herpes simplex virus type I are necessary and sufficient to mediate membrane fusion in a Cos cell transfection system. *J. Virol.* 72:873-875.

60. Visalli, R. J., and C. R. Brandt. 1993. The HSV-1 UL45 18 kDa gene product is a true late protein and a component of the virion. *Virus Res.* 29:167-178.

61. Vivès, E., P. Brodin, and B. Lebleu. 1997. A truncated HIV-1 tat protein basic domain rapidly translocates through the plasma membrane and accumulates in the cell nucleus. *J. Biol. Chem.* 272:16010-16017.

62. Westra, D. F., K. L. Glazenburg, M. C. Harmsen, A. Tiran, A. Jan Scheffer, G. W. Welling, T. Hauw The, and S Welling-Wester. 1997. Glycoprotein H of herpes simplex virus type 1 requires glycoprotein L for transport to the surfaces of insect cells. *J. Virol.* 71:2285-2291.

63. Whitbeck, J. C., C. Peng, H. Lou, R. Xu, S. H. Willis, M. Ponce de Leon, T. Peng, A. V. Nicola, R. I. Montgomery, M. S. Warner, A. M. Soulika, L. A. Spruce, W. T. Moore, J. D. Lambris, P. G. Spear, G. H. Cohen, and R. J. Eisenberg. 1997. Glycoprotein D of herpes simplex virus (HSV) binds directly to HVEM, a member of the tumor necrosis factor receptor superfamily and a mediator of HSV entry. *J. Virol.* 71:6083-6093.

64. White, J. 1992. Membrane fusion. *Science* 258:917-923.

65. Whitley, R. J. 1982. Epidemiology of herpes simplex viruses, p. 1-44. In B. Roizman, (ed), The Herpesviruses, Volume 3. Plenum Press, New York, N.Y.

66. Wild C, T. Oas, C. McDanal, D. Bolognesi, and T. Matthews. 1992. A synthetic peptide inhibitor of human immunodeficiency virus replication: Correlation between solution structure and viral inhibition. *Proc. Natl. Acad. Sci. USA* 89:10537-10541.

67. WuDunn, D., and P. G. Spear. 1989. Initial interaction of herpes simplex virus with cells is binding to heparan sulfate. *J. Virol.* 63:52-58.

68. Yao, Q and R. W. Compans. 1996. Peptides corresponding to the heptad repeat sequence of human parainfluenza virus fusion protein are potent inhibitors of virus infection. *Virology* 223:103-112.

---

What is claimed is:

1. A peptide according to formula 2 (SEQ ID NO: 15)

$(X1)_n$-P-A-V-L-L-A-L-L-A-$(X2)_m$  formula 2 wherein X1 and X2 are selected from one or more charged amino acid residues selected from the group consisting of arginine, lysine and combinations thereof, further wherein n has a value of 0 or 3-10 and m has a value of 0 or 3-10 and wherein either m=0 or n=0.

2. The peptide of claim 1, wherein X1 and X2 are selected from one or more positively charged amino acid residues such that each X1 and each X2 may be the same or different positively charged amino acid residues.

3. The peptide of claim 1, wherein the peptide has a sequence according to SEQ ID NO: 21.

4. A composition comprising the peptide of claim 1 and a pharmaceutically acceptable carrier.

5. The composition of claim 4, wherein the composition is effective for treating herpes simplex virus type 1 ocular disease.

6. A composition comprising the peptide of claim 3 and a pharmaceutically acceptable carrier.

7. A method of treating a herpes simplex virus type-1 ocular infection in a warm blooded animal comprising administering to the animal an effective amount of the composition according to claim 4.

* * * * *